(12) United States Patent
Schulz et al.

(10) Patent No.: US 7,863,052 B2
(45) Date of Patent: Jan. 4, 2011

(54) GRATING-BASED SENSOR COMBINING LABEL-FREE BINDING DETECTION AND FLUORESCENCE AMPLIFICATION AND READOUT SYSTEM FOR SENSOR

(75) Inventors: Stephen C. Schulz, Lee, NH (US); Brian T. Cunningham, Champaign, IL (US); Lance G. Laing, Belmont, MA (US); Peter Y. Li, Andover, MA (US); Brant Binder, Chestnut Hill, MA (US); Gangadhar Jogikalmath, Cambridge, MA (US); Alex Borsody, Lowell, MA (US)

(73) Assignee: SRU Biosystems, Inc., Woburn, MA (US)

( * ) Notice: Subject to any disclaimer, the term of this patent is extended or adjusted under 35 U.S.C. 154(b) by 906 days.

(21) Appl. No.: 11/490,556

(22) Filed: Jul. 20, 2006

(65) Prior Publication Data

US 2010/0227769 A1    Sep. 9, 2010

Related U.S. Application Data

(60) Provisional application No. 60/707,579, filed on Aug. 11, 2005, provisional application No. 60/713,694, filed on Sep. 2, 2005, provisional application No. 60/778,160, filed on Feb. 28, 2006, provisional application No. 60/790,207, filed on Apr. 7, 2006.

(51) Int. Cl.
*G01N 33/551* (2006.01)
(52) U.S. Cl. .................. 436/164; 436/172; 436/518; 436/524; 436/525; 436/527; 436/805
(58) Field of Classification Search .......... None
See application file for complete search history.

(56) References Cited

U.S. PATENT DOCUMENTS

| | | | |
|---|---|---|---|
| 5,216,680 A | 6/1993 | Magnusson et al. | 372/20 |
| 5,504,337 A | 4/1996 | Lakowicz et al. | 250/461.1 |
| 6,078,705 A | 6/2000 | Neuschäfer et al. | 385/12 |
| 6,159,750 A | 12/2000 | Edmonds | 436/537 |
| 6,207,397 B1 | 3/2001 | Lynch et al. | 435/7.8 |
| 6,289,114 B1 | 9/2001 | Neuschäfer et al. | 385/12 |
| 6,395,558 B1 | 5/2002 | Duveneck et al. | 436/172 |
| 6,432,632 B2 | 8/2002 | Nakayama et al. | 435/5 |
| 6,448,018 B1 | 9/2002 | Nakayama et al. | 435/7.1 |
| 6,455,861 B1 | 9/2002 | Hoyt | 250/458.1 |
| 6,566,143 B2 | 5/2003 | Hoyt | 436/172 |
| 6,707,561 B1 | 3/2004 | Budach et al. | 356/521 |
| 6,785,433 B2 * | 8/2004 | Tiefenthaler | 385/12 |
| 6,870,630 B2 | 3/2005 | Budach et al. | 356/521 |
| 7,167,615 B1 | 1/2007 | Wawro et al. | 385/37 |
| 7,400,399 B2 | 7/2008 | Wawro et al. | 356/328 |
| 2002/0110839 A1 | 8/2002 | Bach et al. | 435/7.9 |
| 2002/0127565 A1 | 9/2002 | Cunningham et al. | 435/6 |
| 2002/0135780 A1 | 9/2002 | Budach et al. | 356/521 |
| 2003/0017581 A1 | 1/2003 | Li et al. | 435/287.2 |
| 2003/0027327 A1 | 2/2003 | Cunningham et al. | 435/287.2 |
| 2003/0027328 A1 | 2/2003 | Cunningham et al. | 435/287.2 |
| 2003/0032039 A1 | 2/2003 | Cunningham et al. | 435/6 |
| 2003/0059855 A1 | 3/2003 | Cunningham et al. | 435/7.9 |
| 2003/0077660 A1 | 4/2003 | Pien et al. | 435/7.1 |
| 2004/0130787 A1 | 7/2004 | Thome-Forster et al. | 340/825 |
| 2004/0223881 A1 | 11/2004 | Cunningham et al. | 422/82.05 |
| 2005/0025421 A1 | 2/2005 | Caracci et al. | 385/37 |
| 2005/0053974 A1 | 3/2005 | Lakowicz et al. | 435/6 |
| 2006/0193550 A1 | 8/2006 | Wawro et al. | 385/12 |

FOREIGN PATENT DOCUMENTS

| | | |
|---|---|---|
| WO | WO98/09156 | 3/1998 |
| WO | WO 2004046724 | 6/2004 |

OTHER PUBLICATIONS

Cunningham et al. "A plastic colorimetric resonant optical biosensor for multiparallel detection of label-free biochemical interactions", Sensors and Actuators B, 85 No. 3, pp. 219-226 (Jul. 25, 2002).

(Continued)

*Primary Examiner*—Christopher L Chin
(74) *Attorney, Agent, or Firm*—McDonnell Boehnen Hulbert & Berghoff LLP

(57) ABSTRACT

A grating-based sensor is disclosed that has a grating structure constructed and designed for both evanescent resonance (ER) fluorescence detection and label-free detection applications. Some embodiments are disclosed which are optimized for ER detection in an air mode, in which the sample is dry. Other embodiments are optimized for ER detection in liquid mode, in which the sample is suspended in liquid medium such as water. One and two-dimensional gratings are also disclosed, including gratings characterized by unit cells with central posts, central holes, and two-level, two-dimensional gratings. A readout system for such sensors is also disclosed. One embodiment includes a first light source optimized for collecting label-free detection data, a second light source optimized for collecting ER fluorescence amplification data, and at least one detector. In one embodiment, the detector is an imaging system and includes a CCD camera for collecting both ER and label-free data. In other embodiments, the at least one detector takes the form of a spectrometer for collection of label-free data and a photomultiplier for collecting ER data. In other embodiments, a single light source such as a tunable laser or broad band light source is used.

27 Claims, 24 Drawing Sheets

OTHER PUBLICATIONS

PCT International Search Report and Written Opinion for PCT application No. PCT/US2006/028473, application of SRU Biosystems, Inc., dated Jan. 2, 2007.

Cunningham et al. "*Colorimetric resonant reflection as a direct biochemical assay technique*", Sensors and Actuators B, 81: pp. 316-328 (2002).

Cunningham et al. "*A plastic colorimetric resonant optical biosensor for multiparallel detection of label-free biochemical interactions*", Sensors and Actuators B, 85: pp. 219-226 (2002).

Haes et al., "*A Nanoscale Optical Biosensor: Sensitivity and Selectivity of an Approach Based on the Localized Surface Plasmon Resonance Spectroscopy of Triangular Silver Nanoparticles*", Journal of the American Chemical Society, vol. 124 No. 35 pp. 10596-10604 (2002).

Li et al., "*A new method for label-free imaging of biomolecular interactions*", Sensors and Actuators B,2003.

Cantor et al., "Techniques for the Study of Biological Structure and Function", Biophysical Chemistry Part II, p. 443, (1980).

International Preliminary Report on Patentability dated Jul. 6, 2007 in PCT/US2006/028473 filed Jul. 20, 2006.

Office Action in European Patent Application No. 06 824 773.3 dated May 23, 2008.

Wawro et al., *Optical Fiber Endface Biosensor Based on Resonances in Dielectric Waveguide Gratings*, International Biomedical Optics Symposium Jan. 2000, Proceedings SPIE, vol. 3911, pp. 86-94 (2000).

Extended European Search Report in European Application No. 10161857.7 dated Jun. 16, 2010.

\* cited by examiner

Transmission v. Theta for NovaChip and ComBind 400 air TM Simulation

Reflection v. Wavelength, ComBIND 400, ER Mode in Air (FWHM = 15.6 nm) & BIND Mode in Water (FWHM = 0.5nm)

1D Structure
Grating Depth = 30 nm
TiO$_2$ Thickness = 110nm
Period = 356 nm

X-direction for Bind
Y-direction for ER

Grating Depth = 355 nm
TiO₂ Thickness = 78 nm
X-Period = 550 nm
Y-Period = 432 nm BIND Spectral Resonance, Post Design

GRATING-BASED SENSOR COMBINING LABEL-FREE BINDING DETECTION AND FLUORESCENCE AMPLIFICATION AND READOUT SYSTEM FOR SENSOR

PRIORITY

This application claims priority benefits under 35 U.S.C. §119 (e) to the following United States provisional patent applications, the entire contents of which are incorporated by reference herein:
(1) Ser. No. 60/707,579 filed Aug. 11, 2005
(2) Ser. No. 60/713,694 filed Sep. 2, 2005
(3) Ser. No. 60/778,160 filed Feb. 28, 2006
(4) Ser. No. 60/790,207 filed Apr. 7, 2006.

BACKGROUND

A. Field of the Invention

This invention relates generally to grating-based biochemical sensor devices and detection instruments for such devices. Grating-based sensors are typically used for optical detection of the adsorption of a biological material, such as DNA, protein, viruses or cells, small molecules, or chemicals, onto a surface of the device or within a volume of the device. The sensor of this invention has a grating structure that is constructed in a manner for use in two different applications: (a) label-free binding detection, and (b) fluorescence detection, for example wherein the sample is bound to a fluorophore or emits native fluorescence.

B. Description of Related Art

1. Label-Free Detection Sensors

Grating-based sensors represent a new class of optical devices that have been enabled by recent advances in semiconductor fabrication tools with the ability to accurately deposit and etch materials with precision less than 100 nm.

Several properties of photonic crystals make them ideal candidates for application as grating-type optical biosensors. First, the reflectance/transmittance behavior of a photonic crystal can be readily manipulated by the adsorption of biological material such as proteins, DNA, cells, virus particles, and bacteria on the crystal. Other types of biological entities which can be detected include small and smaller molecular weight molecules (i.e., substances of molecular weight<1000 Daltons (Da) and between 1000 Da to 10,000 Da), amino acids, nucleic acids, lipids, carbohydrates, nucleic acid polymers, viral particles, viral components and cellular components such as but not limited to vesicles, mitochondria, membranes, structural features, periplasm, or any extracts thereof. These types of materials have demonstrated the ability to alter the optical path length of light passing through them by virtue of their finite dielectric permittivity. Second, the reflected/transmitted spectra of photonic crystals can be extremely narrow, enabling high-resolution determination of shifts in their optical properties due to biochemical binding while using simple illumination and detection apparatus. Third, photonic crystal structures can be designed to highly localize electromagnetic field propagation, so that a single photonic crystal surface can be used to support, in parallel, the measurement of a large number of biochemical binding events without optical interference between neighboring regions within <3-5 microns. Finally, a wide range of materials and fabrication methods can be employed to build practical photonic crystal devices with high surface/volume ratios, and the capability for concentrating the electromagnetic field intensity in regions in contact with a biochemical test sample. The materials and fabrication methods can be selected to optimize high-volume manufacturing using plastic-based materials or high-sensitivity performance using semiconductor materials.

Representative examples of grating-type biosensors in the prior art are disclosed in Cunningham, B. T., P. Li, B. Lin, and J. Pepper, *Colorimetric resonant reflection as a direct biochemical assay technique*. Sensors and Actuators B, 2002. 81: p. 316-328; Cunningham, B. T., J. Qiu, P. Li, J. Pepper, and B. Hugh, *A plastic colorimetric resonant optical biosensor for multiparallel detection of label free biochemical interactions*, Sensors and Actuators B, 2002. 85: p. 219-226; Haes, A. J. and R. P. V. Duyne, *A Nanoscale Optical Biosensor: Sensitivity and Selectivity of an Approach Based on the Localized Surface Plasmon Resonance Spectroscopy of Triangular Silver Nanoparticles*. Journal of the American Chemical Society, 2002. 124: p. 10596-10604.

The combined advantages of photonic crystal biosensors may not be exceeded by any other label-free biosensor technique. The development of highly sensitive, miniature, low cost, highly parallel biosensors and simple, miniature, and rugged readout instrumentation will enable biosensors to be applied in the fields of pharmaceutical discovery, diagnostic testing, environmental testing, and food safety in applications that have not been economically feasible in the past.

In order to adapt a photonic bandgap device to perform as a biosensor, some portion of the structure must be in contact with a test sample. Biomolecules, cells, proteins, or other substances are introduced to the portion of the photonic crystal and adsorbed where the locally confined electromagnetic field intensity is greatest. As a result, the resonant coupling of light into the crystal is modified, and the reflected/transmitted output (i.e., peak wavelength) is tuned, i.e., shifted. The amount of shift in the reflected output is related to the amount of substance present on the sensor. The sensors are used in conjunction with an illumination and detection instrument that directs light into the sensor and captures the reflected or transmitted light. The reflected or transmitted light is fed to a spectrometer that measures the shift in the peak wavelength.

The ability of photonic crystals to provide high quality factor (Q) resonant light coupling, high electromagnetic energy density, and tight optical confinement can also be exploited to produce highly sensitive biochemical sensors. Here, Q is a measure of the sharpness of the peak wavelength at the resonant frequency. Photonic crystal biosensors are designed to allow a test sample to penetrate the periodic lattice, and to tune the resonant optical coupling condition through modification of the surface dielectric constant of the crystal through the attachment of biomolecules or cells. Due to the high Q of the resonance, and the strong interaction of coupled electromagnetic fields with surface-bound materials, several of the highest sensitivity biosensor devices reported are derived from photonic crystals. See the Cunningham et al. papers cited previously. Such devices have demonstrated the capability for detecting molecules with molecular weights less than 200 Daltons (Da) with high signal-to-noise margins, and for detecting individual cells. Because resonantly-coupled light within a photonic crystal can be effectively spatially confined, a photonic crystal surface is capable of supporting large numbers of simultaneous biochemical assays in an array format, where neighboring regions within ~10 µm of each other can be measured independently. See Li, P., B. Lin, J. Gerstenmaier, and B. T. Cunningham, *A new method for label-free imaging of biomolecular interactions*. Sensors and Actuators B, 2003.

There are many practical benefits for label-free biosensors based on photonic crystal structures. Direct detection of biochemical and cellular binding without the use of a fluorophore, radioligand or secondary reporter removes experimental uncertainty induced by the effect of the label on molecular conformation, blocking of active binding epitopes, steric hindrance, inaccessibility of the labeling site, or the inability to find an appropriate label that functions equivalently for all molecules in an experiment. Label-free detection methods greatly simplify the time and effort required for assay development, while removing experimental artifacts from quenching, shelf life, and background fluorescence. Compared to other label-free optical biosensors, photonic crystals are easily queried by simply illuminating at normal incidence with a broadband light source (such as a light bulb or LED) and measuring shifts in the reflected color. The simple excitation/readout scheme enables low cost, miniature, robust systems that are suitable for use in laboratory instruments as well as portable handheld systems for point-of-care medical diagnostics and environmental monitoring. Because the photonic crystal itself consumes no power, the devices are easily embedded within a variety of liquid or gas sampling systems, or deployed in the context of an optical network where a single illumination/detection base station can track the status of thousands of sensors within a building. While photonic crystal biosensors can be fabricated using a wide variety of materials and methods, high sensitivity structures have been demonstrated using plastic-based processes that can be performed on continuous sheets of film. Plastic-based designs and manufacturing methods will enable photonic crystal biosensors to be used in applications where low cost/assay is required, that have not been previously economically feasible for other optical biosensors.

The assignee of the present invention has developed a photonic crystal biosensor and associated detection instrument for label-free binding detection. The sensor and detection instrument are described in the patent literature; see U.S. patent application publications U.S. 2003/0027327; 2002/0127565, 2003/0059855 and 2003/0032039. Methods for detection of a shift in the resonant peak wavelength are taught in U.S. Patent application publication 2003/0077660. The biosensors described in these references include 1- and 2-dimensional periodic structured surfaces applied to a continuous sheet of plastic film or substrate. The crystal resonant wavelength is determined by measuring the peak reflectivity at normal incidence with a spectrometer to obtain a wavelength resolution of 0.5 picometer. The resulting mass detection sensitivity of <1 pg/mm$^2$ (obtained without 3-dimensional hydrogel surface chemistry) has not been demonstrated by any other commercially available biosensor.

A fundamental advantage of the biosensor devices described in the above-referenced patent applications is the ability to mass-manufacture with plastic materials in continuous processes at a 1-2 feet/minute rate. Methods of mass production of the sensors are disclosed in U.S. Patent application publication 2003/0017581. As shown in FIG. 1, the periodic surface structure of a biosensor 10 is fabricated from a low refractive index material 12 that is overcoated with a thin film of higher refractive index material 14. The low refractive index material 12 is bonded to a base sheet of clear plastic material 16. The surface structure is replicated within a layer of cured epoxy 12 from a silicon-wafer "master" mold (i.e. a negative of the desired replicated structure) using a continuous-film process on a polyester substrate 16. The liquid epoxy 12 conforms to the shape of the master grating, and is subsequently cured by exposure to ultraviolet light. The cured epoxy 12 preferentially adheres to the sheet 16, and is peeled away from the silicon wafer. Sensor fabrication was completed by sputter deposition of 120 nm titanium oxide ($TiO_2$) high index of refraction material 14 on the cured epoxy 12 grating surface. Following titanium oxide deposition, 3×5-inch microplate sections are cut from the sensor sheet, and attached to the bottoms of bottomless 96-well and 384-well microtiter plates with epoxy.

As shown in FIG. 2, the wells 20 defining the wells of the mircotiter plate contain a liquid sample 22. The combination of the bottomless microplate and the biosensor structure 10 is collectively shown as biosensor apparatus 26. Using this approach, photonic crystal sensors are mass produced on a square-yardage basis at very low cost.

The detection instrument for the photonic crystal biosensor is simple, inexpensive, low power, and robust. A schematic diagram of the system is shown in FIG. 2. In order to detect the reflected resonance, a white light source illuminates a ~1 mm diameter region of the sensor surface through a 100 micrometer diameter fiber optic 32 and a collimating lens 34 at nominally normal incidence through the bottom of the microplate. A detection fiber 36 is bundled with the illumination fiber 32 for gathering reflected light for analysis with a spectrometer 38. A series of 8 illumination/detection heads 40 are arranged in a linear fashion, so that reflection spectra are gathered from all 8 wells in a microplate column at once. See FIG. 3. The microplate+biosensor 10 sits upon a X-Y addressable motion stage (not shown in FIG. 2) so that each column of wells in the microplate can be addressed in sequence. The instrument measures all 96 wells in ~15 seconds, limited by the rate of the motion stage. Further details on the construction of the system of FIGS. 2 and 3 are set forth in the published U.S. Patent Application 2003/0059855.

The descriptions and discussions below refer to the label-free technology described above as BIND technology. BIND is a trademark of the assignee SRU Biosystems, Inc.

2. Fluorescence Amplification Sensors

U.S. Pat. No. 6,707,561 describes a grating-based biosensing technology that is sometimes referred to in the art as Evanescent Resonance (ER) technology. This technology employs a sub-micron scale grating structure to amplify a luminescence signal (e.g., fluorescence, chemi-luminescence, electroluminescence, phosphorescence signal), following a binding event on the grating surface, where one of the bound molecules carries a fluorescent label. ER technology enhances the sensitivity of fluorophore based assays enabling binding detection at analyte concentrations significantly lower than non-amplified assays.

ER technology uses grating generated optical resonance to concentrate laser light on the grating surface where binding has taken place. In practice, a laser scanner sweeps the sensor at some angle of incidence (theta), typically from above the grating, while a detector detects fluoresced light (at longer optical wavelength) from the sensor surface. By design, ER grating optical properties result in nearly 100% reflection, also known as resonance, at a specific angle of incidence and laser wavelength ($\lambda$). Confinement of the laser light by and within the grating structure amplifies emission from fluorophores bound within range of the evanescent field (typically 1-2 um). Hence, at resonance, transmitted light intensity drops to near zero.

As noted above, the label-free biosensors described in the above-referenced patent applications employ a sub-micron scale grating structure but typically with a significantly different grating geometry and objective as compared to gratings intended for ER use. In practical use, label-free and ER technologies have different requirements for optical characteristics near resonance. The spectral width and location of the resonance phenomena describes the primary difference. Resonance width refers to the full width at half maximum, in wavelength measure, of a resonance feature plotted as reflectance (or transmittance) versus wavelength (also referred to as Q factor above). Resonance width can also refer to the width, in degrees, of a resonance feature plotted on a curve representing reflectance or transmittance as a function of theta, where theta is the angle of incident light.

Optimally, a label-free grating-based sensor produces as narrow a resonance peak as possible, to facilitate detection of small changes in peak position indicating low binding events. A label-free sensor also benefits from a high grating surface area in order to bind more material. In current practice, one achieves higher surface area by making the grating deeper (though other approaches exist). Current commercial embodiments of label-free sensors produce a resonance near 850 nm, thus BIND label-free detection instrumentation has been optimized to read this wavelength.

Conversely, practical ER grating sensor designs employ a relatively broad resonance to ensure that resonance occurs at the fixed wavelength laser light and often fixed angle of incidence in the presence of physical variables such as material accumulation on the grating or variation in sensor manufacture. Because field strength generally decreases with resonance width, practical ER sensor design calls for a balance in resonance width. By choosing an appropriate ER resonance width, one ensures consistent amplification across a range of assay, instrument and sensor variables while maintaining ER signal gain. A typical application uses a 633 nm wavelength to excite a popular fluorescent dye, known in the art as Cy5. Some ER scanning instrumentation permits adjustments to incident angle to "tune" the resonance towards maximum laser fluorophore coupling. This practice, however, may induce an unacceptable source of variation without proper controls.

Known ER designs also employ more shallow grating depths than optimal label-free designs. For example, the above-referenced '561 patent specifies the ratio of grating depth to "transparent layer" (i.e., high index coating layer) thickness of less than 1 and more preferably between 0.3 and 0.7. Optimal label-free designs employ gratings with a similarly defined ratio of greater than 1 and preferably greater than 1.5. Label-free designs typically define grating depth in terms of the grating line width or half period. For example, currently practiced commercial label-free sensors have a half period of 275 nm and a grating depth of approximately 275 nm, thus describing a 1:1 geometric ratio. This same sensor design employs a high index of refraction oxide coating on top of the grating with a thickness of approximately 90 nm. Thus, according to the definition in '561 patent, this sensor has a grating depth:oxide thickness ratio of approximately 3:1.

This disclosure reports grating-based sensor designs which are constructed in a manner such that it is optimized for both modes of detection (label-free and fluorescence amplification), in a single device. Such a grating dramatically increases the diversity of applications made possible by a single product.

All the previously cited art is fully incorporated by reference herein.

SUMMARY

The following embodiments and aspects thereof are described and illustrated in conjunction with systems, tools and methods meant to be exemplary and illustrative, not limiting in scope. In various embodiments one or more of the above-described problems have been reduced or eliminated, while other embodiments are directed to other improvements.

In one aspect, a grating-based sensor is disclosed which is optimized for performance in both ER mode and in a label-free detection mode. Such sensors exhibit a broad resonance at small angles of incidence (theta), mimicking the performance curves of a conventional ER grating biosensor, while also maintaining sharp resonance peak in a label-free detection mode. Several representative embodiments are disclosed. A first embodiment is optimized for ER mode in an air sample medium and with TM polarization of light (perpendicular to the grating). A second embodiment is disclosed which is optimized for ER mode in a liquid sample medium with 633 nm excitation, near normal incidence, and with TE polarization. Computer modeling of both embodiments indicates that each maintains sharp peak wavelength resonance (high Q factor) in a label-free detection mode.

In one configuration, a biosensor has a periodic surface grating structure (either in one or two dimensions), wherein the periodic grating structure is constructed so as to optimize optical interrogation of the biosensor from a first light source in an evanescent resonance (ER) detection mode, and wherein the periodic grating structure is constructed so as to optimize optical interrogation of the biosensor with light from a second light source in a label-free detection mode. In one possible embodiment, the grating takes the form of a two-dimensional grating, and wherein the grating is periodic in first and second mutually orthogonal directions. In other embodiments, the grating is a one-dimensional grating, with periodicity in one direction (e.g., the X direction) but not in the second direction.

Label-free detection use of the biosensor benefits from deeper gratings to provide more surface area, enabling more material attachment. More attached material generates more signal in the form of larger shift of the peak wavelength value. Prior ER gratings do not have enough surface area (depth) to render label-free sensitivity equivalent to current label-free grating sensors. Hence, one designs biosensors maximize surface area (translating greater grating depth in this case) while maintaining a broad resonance curve at the intended laser excitation wavelength and low angles of incidence, preferably less than 10 degrees and more preferably less than five degrees. Biosensors meeting ER and label-free performance requirements in representative one-dimensional embodiments have a grating depth to half period ratio of between about 0.6 and about 1.2. Grating depths of between approximately 160 nm and approximately 210 nm are specifically contemplated. These parameters may of course vary to address specific sensor performance objectives, to emphasizing ER or label-free performance, or for example in two-dimensional gratings as disclosed herein.

Computer simulation of grating design, in accordance with the teachings of this disclosure, will allow persons skilled in the art to develop other grating designs in accordance with this disclosure which may vary from the specifics of the first and second embodiments and such embodiments are offered by way of illustration and not limitation. In a further aspect, methods of designing dual use ER and label-free detection biosensors are disclosed using computer modeling techniques.

A grating-based sensor having a two-dimensional orthogonal grating structure suitable for both ER and label-free detection is also disclosed and may be preferred in some implementations. A two-dimensional grating can look like a waffle (holes), a waffle iron (posts), or a chessboard configuration with alternating high and low regions in two dimensions. Two dimensional gratings can have different periods in the X and Y directions. These features may have various profiles in the Z direction such as angled or curved sidewalls. Thus, in the case of the waffle pattern, the impressions or wells may have a rectangular rather than a square shape. In practice, these features will also appear rounded in the X and Y dimensions, i.e., will not have sharp corners. Thus, the use of the terms "rectangular" and "square" are intended to refer to the overall configuration and allow for rounded corners. This added flexibility provided by two dimensional gratings allows one to tune the resonance positions for both label-free detection and ER detection to occur at different wavelengths. This capability offers significant benefit in terms of tuning of the ER resonance to different excitation wavelengths while maintaining compatibility with existing label-free detection instrumentation. As an example, the X periodicity can provide a broad resonance at or near normal incidence with wavelength tuned to excite the Cy3 fluorophore (green light) or the Cy5 fluorophore (red light), while the Y periodicity can yield a sharp label-free resonance between 820 and 850 nm (near infra red) similar to currently commercialized label-free sensors.

Two-dimensional, two-level grating structures are also disclosed as a further embodiment of a grating-based biosensor which is structured and arranged to have good performance for both ER and label-free detection.

In another aspect, a method of analyzing at least one sample is disclosed comprising the steps of placing the at least one sample on a biosensor comprising a substrate having a periodic surface grating structure, wherein the periodic grating structure is constructed and designed for optical interrogation of the biosensor in an evanescent reflection (ER) detection mode as well as optimize optical interrogation of the biosensor in a label-free detection mode. The method further comprises the steps of illuminating the biosensor in a readout detection instrument with light from a light source designed for the ER detection mode and illuminating the biosensor with light from the light source (or possibly from a second light source) designed for the label-free detection mode; and analyzing light reflection from the biosensor. The analyzing of the sample may include detecting binding of a component of the sample, e.g., binding of the component of the sample to the surface of the biosensor or binding of second sample component (e.g., fluorophore, inhibitor or label) to a first sample component (e.g., protein)

In one embodiment, the readout system includes two light sources, one for BIND (e.g., a while light source or light emitting diode) and a second light source such as laser for ER measurements. However, in other embodiments a single light source is provided such as a Xenon discharge lamp or tunable laser, with two (or more) bandpass filters sampling the light source to provide appropriate illumination wavelengths for the two sensing modes.

In one possible embodiment, the sample is in an air medium, and wherein the light from the first light source has a polarization perpendicular to the grating structure. In another possible embodiment, the sample is in a liquid medium, and wherein the light from the first light source has a polarization parallel to the grating structure. In one possible embodiment, light from the first light source has a wavelength selected to activate a fluorophore bound to the sample. In another possible embodiment, light from the first light source has a wavelength selected to activate native fluorescence of the sample. In still other embodiments, a fraction of the sample is bound to an inhibitor, which may include a bound fluorophore. The sample may be, for example, a protein.

Several representative configurations of a readout and detection instrument for the inventive biosensor are also disclosed. In one embodiment, the readout and detection instrument includes a first light source adapted for obtaining ER data from the biosensor; a second light source adapted for obtaining label-free detection data; an optical system combining the light from the first and second light sources into an illuminating beam for illuminating the biosensor; at least one detector for detecting reflected light from the biosensor; and an analysis module using data from the at least one detector and obtaining ER and label-free data from the sample. The detector may be an imaging detector such as a charge-coupled device (CCD imager). Other types of detectors are also envisioned, such as photodetector, spectrometer, or a combination thereof, one for acquiring ER data and one for acquiring BIND data. In another representative configuration, the optical system selectively illuminates the biosensor with light from a single light source. The biosensor may have multiple detection sites or wells, and the instrument may include a motion stage for successively moving the detection sites relative to the light sources to sequentially obtain ER and label-free data from all the detection sites.

In sum, this disclosure describes a novel detection and quantification platform that combines a photonic crystal based label-free biosensor with enhanced fluorescence capabilities, in a single device. Alone, label-free and ER technologies have great utility. The ability to join these two detection technologies in a single biosensor creates a powerful approach for universal detection and selective measurement of interaction between and within biological materials such as cells, proteins, and small molecules. The combined biosensor of this disclosure is useful for detection of a broad range of biological or chemical sample entities. Examples of the types of samples which can be detected include small and smaller molecular weight molecules (i.e., substances of molecular weight<1000 Da and between 1000 Da to 10,000 Da), amino acids, nucleic acids, lipids, carbohydrates, nucleic acid polymers, viral particles, viral components and cellular components such as but not limited to vesicles, mitochondria, membranes, structural features, periplasm, or any extracts thereof.

In general, further examples of specific binding substances (samples) which may be detected with the biosensor of this invention include polypeptides, antigens, polyclonal antibodies, monoclonal antibodies, single chain antibodies (scFv), F(ab) fragments, F(ab')2 fragments, Fv fragments, small organic molecules, cells, viruses, bacteria, polymers, peptide solutions, protein solutions, chemical compound library solutions, single-stranded DNA solutions, double stranded DNA solutions, combinations of single and double stranded DNA solutions, RNA solutions and biological samples. Such biological samples could consists of, for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears and prostatic fluid.

The biosensor described herein may be used to detect (a) binding of components any of these types of samples to the biosensor surface, (b) binding of the sample to another component of the sample, e.g., a fluorophore in the sample, and (c) binding of the sample or sample component to a second sample which is added to the sample. As an example of binding (b), the sensor surface may bind to some component of the sample, such as for example streptavidin-biotin or 6His, and the biosensor may be used to detect the interaction of the bound component of the sample with an additional grouping of components in the sample, such as a polymerase complex. In the latter example of binding (c), a sample may have a component that is attached to the surface of the biosensor and another component which specifically binds/attracts another component(s) from a second sample that is placed on the biosensor.

The sensor of this disclosure may also be used for quantification of the amount of material binding or interaction.

The following general examples by no means represent a complete or exclusive listing of novel utilities enabled by such a dual use grating-based sensor as disclosed herein:

1. Combined, the two technologies distinguish the percentage of fluorophore labeled material present in a mixed sample population. The label-free signal provides a quantitative measure of the total mass bound to the sensor while the ER signal quantifies the presence of the label.

2. The combination can also increase statistical rigor in the measurement of interactions between and within cells, proteins, and small molecules by providing duplicate binding signals from different sources.

3. Utilizing the Förster Resonant Energy Transfer (FRET) principle, the dual use sensor may enable measurement of the distance between two differentially labeled fluorescent molecules or two differentially labeled portions of the same molecule. The label-free signal quantifies molecular density.

4. The combination of the two technologies can provide additive information. The label-less signal can quantify the attachment of cells with the fluorescent signal quantifying the amount of fluorophore labeled ligand bound to the cell. Other scenarios are of course possible where label-less and labeled biological entities, such as those listed above, are detected on the inventive biosensor.

5. The combination of the two technologies may provide a measure of the molecular mass by distinguishing molecular count from total bound mass.

6. The combined biosensor further permits two different independent quantification tests to be performed for other scenarios such as the study of inhibition binding. Furthermore, a more complete understanding and characterization of inhibition binding interactions between a protein and a substrate is possible, including the ability to directly quantify inhibitor ligand binding. As an additional example, the biosensor facilitates the study of very tight binding interactions whereby a known competitive inhibitor with a weaker binding affinity is employed to perturb/observe the much tighter binding entity.

7. The combined ER and label-free biosensor is particularly useful for assays which utilize the natural fluorescence of biological molecules (i.e., without requiring the use of a bound fluorescence label), to make biophysical characterization measurements of activity such as folding, stacking, and changes and rates of changes to these upon interactions with other biological molecules and small test molecules. Such characterization measurements could be made using a bound fluorescence label, but such bound label is not necessarily required, especially for biological materials having an inherent fluorescence property. See Charles R. Cantor and Paul R. Schimmel, parts 1-3 *Biophysical Chemistry—The behavior and study of biological molecules*, W.H. Freeman and Company, New York, (1980), page 443 and table 8-2 for a listing of fluorescence characteristics of protein and nucleic acid constituents and coenzymes, their absorption and emission spectra and sensitivity. This technique of using native fluorescence is especially important with nucleic acid polymers (DNA, RNA) (fluorescent nucleoside bases) stacking and hybridization, proteins (fluorescent amino acids phenylalanine, tryptophan, and tyrosine) and lipid membranes (enhancement and quenching effects upon incorporation of fluorophores into their different compartmentalizations). In one embodiment, the label-free BIND feature allows the quantification of the amount of sample material or ligand bound thereto and the ER feature detects the native fluorescence and allows the sensitive tracking of the biophysical change.

BRIEF DESCRIPTION OF THE DRAWINGS

Exemplary embodiments are illustrated in referenced figures of the drawings. The embodiments and figures disclosed herein are offered by way of example and not limitation. All questions regarding scope of the invention are to be answered by reference to the claims.

DETAILED DESCRIPTION

Grating-based biosensors are disclosed which have a periodic grating construction which is optimized and useful for both ER detection, either in a liquid or dry environment, and for label-free detection. A readout system adapted for use with the biosensors is also described. Methods of testing a sample with the inventive biosensors are also described.

First Embodiment

Figure 4:
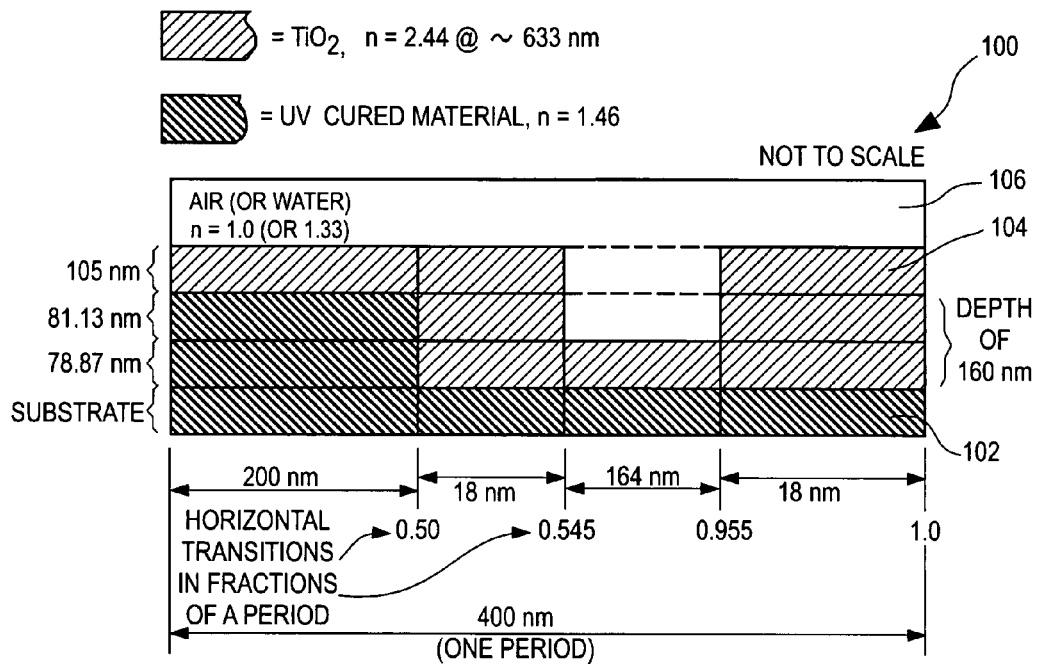
FIG. 4 is a cross-section of a first embodiment of a combined ER and label-free detection biosensor.

FIG. 4 is a schematic cross-sectional illustration of a first embodiment of a one-dimensional sensor having a grating structure 100 that is expected to meet commercial requirements for both ER and label-free applications of a grating-based sensor. FIG. 4 shows one period of a grating structure 100 in one dimension or direction. The dimensions are not to scale in FIG. 4.

The grating 100 of FIG. 4 is superimposed and bonded to a base sheet of clear material such as Polyethylene Terepthalate (PET) or other plastic, glass or other material (not shown).

The grating structure consists of a periodically repeating material 102 which preferably comprises a UV-cured material, e.g., epoxy, applied with the aid of a grating master wafer (not shown) to replicate the grating pattern onto the base sheet of PET material located below the layer "substrate." The UV cured material 102 is applied to a substrate sheet such as PET. Substrate materials can also include polycarbonate or cyclo-olefin polymers such as Zeanor®. Other means of producing the structured layer 102 include thermally stamping directly into a polymer substrate. The middle material 104 represents a sputtered oxide coating with high refractive index (e.g. $TiO_2$ or $Ta_2O_5$). The upper most material 106 represents a medium for a sample, which is normally either a water-based buffer, for label-free detection mode, or air, for ER mode. The structure has the periodicity, layer structure, and horizontal transition points as shown in the Figure. The specifics of the design of course may change while still providing good performance for both label-free detection and ER detection.

The design of FIG. 4 was developed and its performance modeled with the aid of a computer and a software program GSolver (Grating Solver Development Co., Allen Tex., www.gsolver.com). The various geometrical dimensions and parameters, spacing, well depth, materials, and index of refraction data associated with the materials allows the design to be studied on a computer and simulations run to predict the Transmission v. Theta curve and reflection as a function of wavelength curve. Such simulations can be run in situations where the sample is dry and when the sample is suspended in water or other fluid medium with known index of refraction. Such simulations allow the designer to optimize, i.e., change, the various design parameters (thicknesses, transitions, period, etc.) to satisfy the requirements for both ER and label-free detection.

ER technology heretofore employs a resonance mode induced by incident light with a polarization parallel to the grating, defined here as TE mode or polarization. Label-free detection technology typically employs a resonance mode induced by incident light with polarization perpendicular to the grating, defined here as the TM mode or polarization. This mode produces the narrowest resonance when the sample is suspended in a liquid medium.

In the first embodiment of FIG. 4, a grating biosensor design is described which utilizes TM polarization for both label-free detection of a sample suspended in liquid and ER detection in an air (dry) environment. Changing the medium above the grating from water to air results in a change in resonance characteristics from those useful for label-free detection to those useful for ER amplification of dyes responding to 633 nm excitation. The design of FIG. 4 is not specifically optimized to ER detection in a water mode and may not even work acceptably for ER in a water mode. However, many ER detection assays are run in an air environment and so the design of FIG. 4 has much utility for ER detection.

Figure 6:
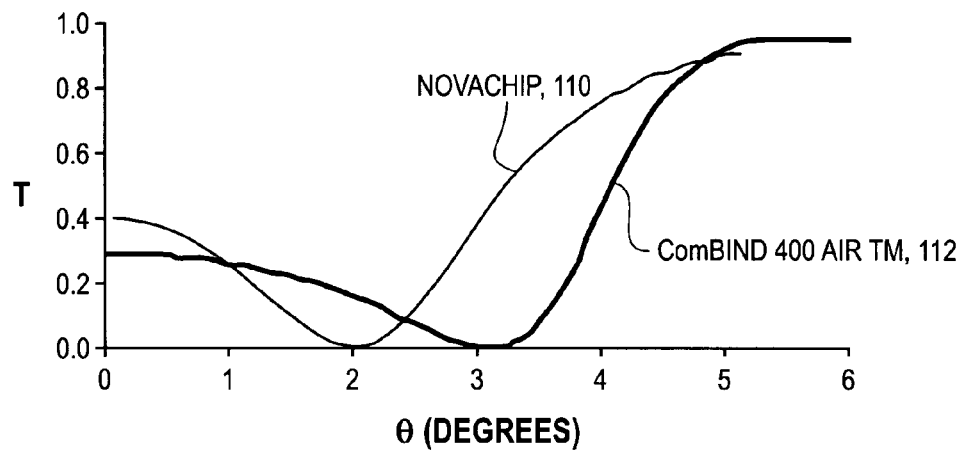
FIG. 6 is a graph comparing transmission as a function of incident angle theta for a prior art ER biosensor ("NovaChip") with a computer simulation of the embodiment of FIG. 4 when used for ER detection in a dry (air) medium environment.

FIG. 6 is a graph that compares Transmission v. Theta data for a prior art ER device (NovaChip, Novartis AG) with a computer simulation or model of the first design of FIG. 4 ("Combind 400 Air"). NovaChip data is disclosed in Budach et al., *Generation of Transducers for Fluorescence-Based Microarrays with Enhanced Sensitivity and Their Application to Gene Expression Profiling*, Analytical Chemistry (2003) and in Neuschafer et al., *Evanescent resonator chips: a universal platform with superior sensitivity for fluorescence-based microarrays*, Biosensors and Bioelectronics 18 (2003) 489-497. The curves 110 and 112 have a similar shape suggesting the simulated device (ComBIND 400) would function equivalently to the ER device. The NovaChip TE resonance occurs at ~2 degrees from normal incidence. The first design of FIG. 4 produces TE resonance at ~3 degrees, which is considered only a minor difference given that one can adjust the angle of incident light (see the discussion of the readout and detection instrument for the sensor later in this disclosure).

Figure 7:
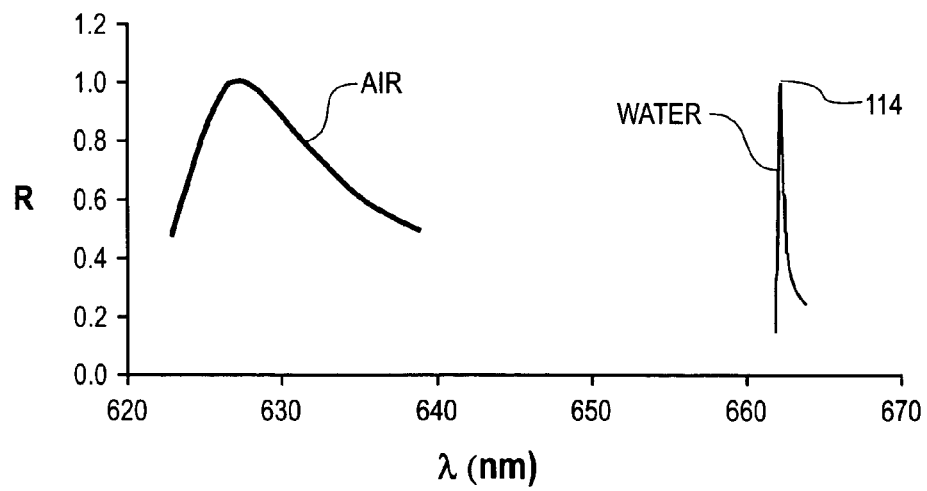
FIG. 7 is a graph comparing reflection as a function of wavelength for the embodiment of FIG. 4 in a label-free detection mode in an aqueous medium environment; the graph of FIG. 7 was generated from a computer simulation of the embodiment of FIG. 4.

The graph of FIG. 7 plots simulated reflection vs. wavelength for the ComBind 400 design (FIG. 4). The broad reflection peak centered around 628 nm corresponds to the ER-air mode resonance occurring at ~3 degrees in the Transmission v. Theta curve above. The narrow peak, labeled "water", serves for the label-free mode of detection. Note the extreme sharpness of the peak 114. This suggests that the design of FIG. 4 would work well for label-free detection in a water environment.

During label-free mode detection, biological molecules adhere to the $TiO_2$ coating and effectively increase the optical thickness of that material. This results in a shift in the peak wavelength value (PWV) of the resonance. A larger PWV shift for a fixed amount of material represents higher detection sensitivity. When comparing grating designs in a computer simulation, the simulation of additional biological material can be modeled by incrementing the thickness of the $TiO_2$ layer rather than adding a hypothetical biological layer. This method has proven effective in other grating design exercises.

Figure 8:
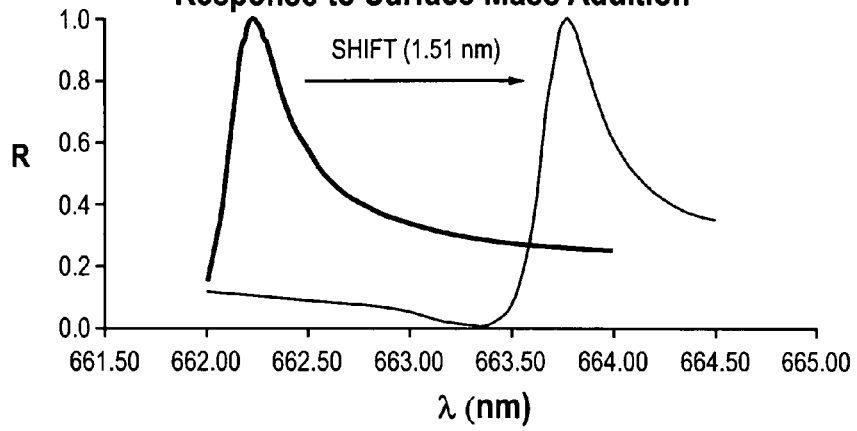
FIG. 8 is a graph of reflection as a function of wavelength for the embodiment of FIG. 4 in a label-free detection mode, showing a shift of the peak wavelength value in response to surface mass addition (e.g., by adding a sample to the biosensor). The graph of FIG. 7 was also generated via a computer simulation of the embodiment of FIG. 4.

FIG. 8 is a graph that plots the peak wavelength value in a water environment before and after the addition of a certain amount of simulated mass (simulated by increasing the thickness of the $TiO_2$ layer 104 of FIG. 4). The peak position shifts to higher wavelength, as is expected in label-free biosensor operation. The ratio of wavelength shift to simulated mass is equivalent to that of the commercialized biosensors of the applicant's assignee. Hence, the grating of FIG. 4 is expected to yield equivalent label-free performance to the current label-free biosensor gratings.

To summarize, simulations predict dual-use capabilities for the grating design disclosed in FIG. 4. When dry, it can amplify fluorescent binding signals according to the technology known as evanescent resonance (ER). When wet, the grating performs as well as a label-free detector according to the technology known as guided mode resonance detection or commercially as BIND (trademark of SRU Biosystems, Inc.), available from the applicants' assignee SRU Biosystems, Inc.

Second Embodiment

Figure 5:
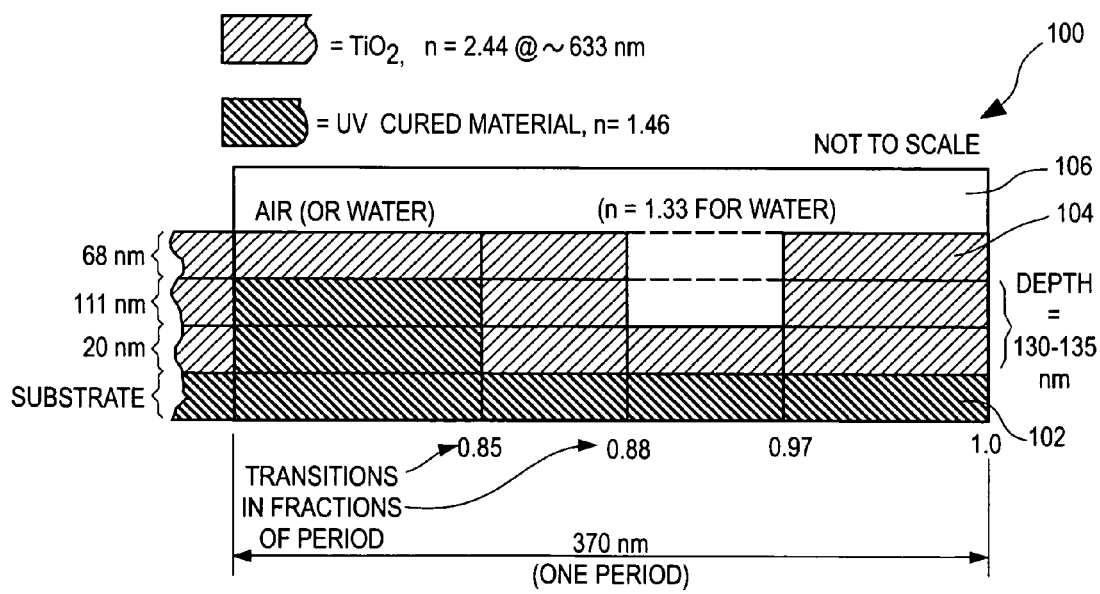
FIG. 5 is a cross-section of a second embodiment of a combined ER and label-free detection biosensor.

FIG. 5 is a cross-section of a second embodiment, showing one period of the grating structure in one dimension and the structure of the of the UV cured layer 102, the high index of refraction layer 104, and the sample medium 106. The dimensions and transition points are as shown in the drawing. The drawing is not to scale.

The design of FIG. 5 differs from that of FIG. 4 is several respects:

a) It has a shorter grating period.

b) It has narrower grating troughs or recesses. The "duty cycle" (percentage of the grating at the upper level in a unit cell) is 88% in FIG. 5 (0 to 0.85 and 0.97 to 1.0). Narrow troughs with duty cycles of between 70 and 95% are exemplary of the narrow trough embodiments. The narrow troughs generally give better label-free detection results. The narrow trough feature narrows the TE resonance peak, thus indicating increased field strength. While practical use of the ER effect requires a sufficiently broad resonance, a resonance with excessive width will have insufficient field strength to produce useful fluorescence signal amplification c) It has a 1:1 ratio of grating depth to half period.

Figure 9:
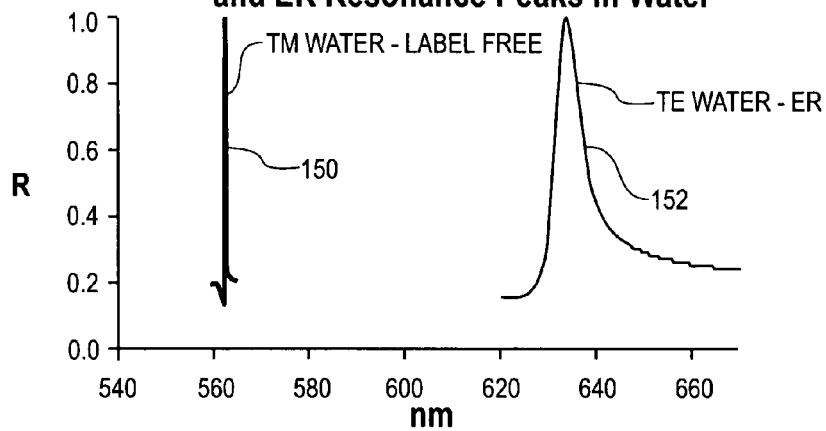
FIG. 9 is a graph of reflection on as a function of wavelength showing the resonance peaks for the embodiment of FIG. 5 in label-free and ER detection modes. The graph was generated from a computer simulation of the embodiment of FIG. 5.
Figure 10:
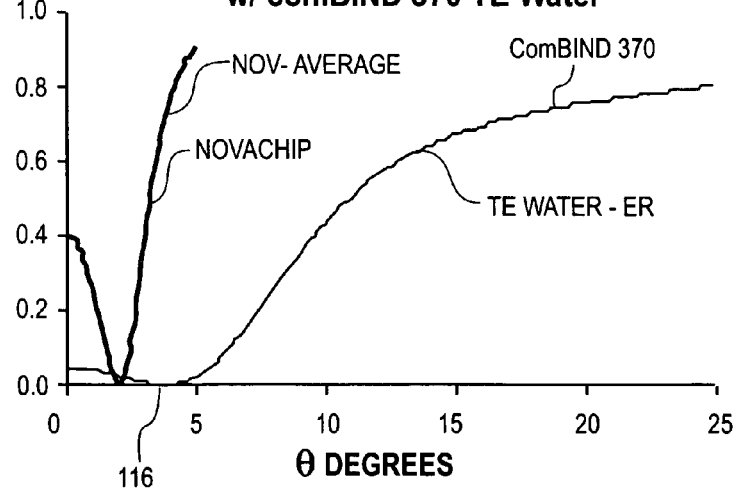
FIG. 10 is a graph of transmission as a function of theta for the embodiment of FIG. 5 and comparing the curve with the transmission curve of a prior art "NovaChip" example of an ER sensor.

The design of FIG. 5 exemplifies a one-dimensional sensor that enables both label-free and ER operation in a water (or buffer) environment. This contrasts with the design of FIG. 4, which is designed for ER operation in air and label-free operation in water. The graph of FIG. 9 shows the ER (TE polarization) and comparatively narrow label-free (TM polarization) spectral resonance characteristics in a water environment for the design of FIG. 5. The graph was generated from a computer simulation of the embodiment of FIG. 5. The graph of FIG. 10 compares the TE angular resonance, using 633 nm excitation, of the FIG. 5 design ("ComBIND 370") as compared to a prior art NovaChip. In this case, the simulated transmission minimum 116 occurs below five degrees angle of incidence, close to that of the existing NovaChip ER device. The incident angle, period, excitation wavelength, high index of refraction material thickness, grating duty cycle, and grating depth all interrelate. Excitation wavelengths for commercial fluorophores are known and can be looked up. Angles of incidence of less than 25 degrees should be acceptable but angles near normal (Theta close to zero) are preferred. With angle and wavelength confined to narrow ranges, designing a grating with functional and commercially useful ER and label-free performance one must determine a grating period, duty cycle, depth and high index of refraction material thickness that result in high PWV shift in response to mass attachment, for label-free use, and high surface field at the excitation wavelength of the specified fluorophore or dye for ER mode. Additionally, the design must produce a label-free resonance with spectral width as narrow as possible while maintaining an ER resonance with angular width enough to yield a practical parameter window for measurement. The design may incorporate performance trade-offs. For example, optimization of ER performance engages a trade-off between field strength, which yields signal amplification, and tolerance for sensor, instrument and assay variables. Narrower ER resonance generally indicates higher field strength while broader ER resonance provides increased measurement tolerance. Typically, label-free and ER performance optimization involves another trade-off between grating depth, which enhances label-free performance, and ER resonance width. For example, in the case of the design of FIG. 5, increasing the grating depth widens the TE/ER resonance beyond optimum. Increasing the duty cycle (narrowing the troughs) compensates, narrowing the resonance back towards optimum, and thus maintaining field ER strength.

Thus, one preferred approach to finding a dual use granting structure for both ER and label-free detection modes involves finding a grating with depth to half period ratio approximately in the range of 0.6 to 1.2 or more that also yields a broad angular resonance in either TM mode in an air environment, TE mode in air environment, or TE mode in a water environment, at the excitation wavelength of interest (e.g., 633 nm) and a resonance angle less than 25 degrees. This broad resonance preferably has a width between 1 degree and 10 degrees or, in terms of spectral width, between 5 nm and 30 nm. Such design efforts can be readily implemented in a computer, e.g., using the Gsolver software. More directly, one can comparatively model field strength at the grating surface using a software such as R-Soft, available from RSoft Design Group, www.rsoftdesigngroup.com.

Grating depths in the range of 100 to 600 nm and grating periods in the range of 300 to 600 nm are considered exemplary.

Persons skilled in the art having the benefit of this disclosure will be able to model potential grating designs on a computer and arrive at suitable designs in accordance with this invention.

Two-Dimensional Gratings

The possibility of a two-dimensional (2-D) grating structure, suitable for both ER and label-free detection, is also contemplated and may be preferred. A two-dimensional grating can look like a waffle (holes), a waffle iron (posts), or a chessboard configuration with alternating high and low regions in two dimensions. Two-dimensional gratings can have different periods in the X and Y directions. These features may have various profiles in the Z direction such as angled or curved sidewalls. Thus, in the case of the waffle pattern, the impressions or wells may have a rectangular rather than a square shape. This added flexibility allows one to tune the resonance positions for both label-free detection and ER detection to occur at different wavelengths. This flexibility offers significant benefit in terms of tuning the ER resonance to different excitation wavelengths while maintaining compatibility with existing label-free detection instrumentation. As an example, the X periodicity can provide a resonance at or near normal incidence with wavelength tuned to excite the CY3 fluorophore (green light) or the CY5 fluorophore (red light), while the Y periodicity can yield a resonance fixed between 820 and 850 nm (in the near infra red).

The examples of 2-D biosensor structures described herein were developed using computer simulations and Rigorous Coupled Wave Analysis (RCWA) with a commercially available software package (RSoft). The computer simulations enable the device designer to vary the physical parameters of the device (refractive index, thickness, width, height, structural shape) to determine: 1) the electromagnetic field distribution within and around the device, 2) the reflectance or transmittance behavior as a function of incident angle of light and wavelength of light, and 3) how the reflected (or transmitted) spectrum is changed by the attachment of biomolecular material to the surface of the biosensor.

The specific 2-D embodiments described herein are optimized for combined detection by BIND and ER methods in a single device where the sensor contacts water during the BIND measurement and air during the ER measurement. Any combination of dry and wet for BIND and ER may be similarly optimized (e.g., measure both BIND and ER in a wet mode).

To more fully appreciate the advantages provided by the combined ER and BIND (label-free) two-dimensional device, a discussion will initially be presented in conjunction with FIGS. 11-14 of a linear (one-dimensional) structure optimized for ER only. Simulations were first performed on the ER-only structure. The structure corresponds approximately to a prior art ER chip published by Budach et al., *Generation of Transducers for Fluorescence-Based Microarrays with Enhanced Sensitivity and Their Application for Gene Expression Profiling*, Anal Chem 2003, 75, 2571-2577. (Note: The Budach et al. grating is a linear grating and so is a 1-D structure as that term is used herein. The thinner $TiO_2$ high index of refraction of material of FIGS. 11A-11B as compared to the thicker $Ta_2O_5$ layer described by Budach et al. paper achieves a device of equivalent optical "thickness" by taking into account the different indices of refraction of the two materials. The modeling of FIGS. 11A-11B is not meant to exactly replicate the Budach et al. device, but rather to approximate it.)

Figure 11A:
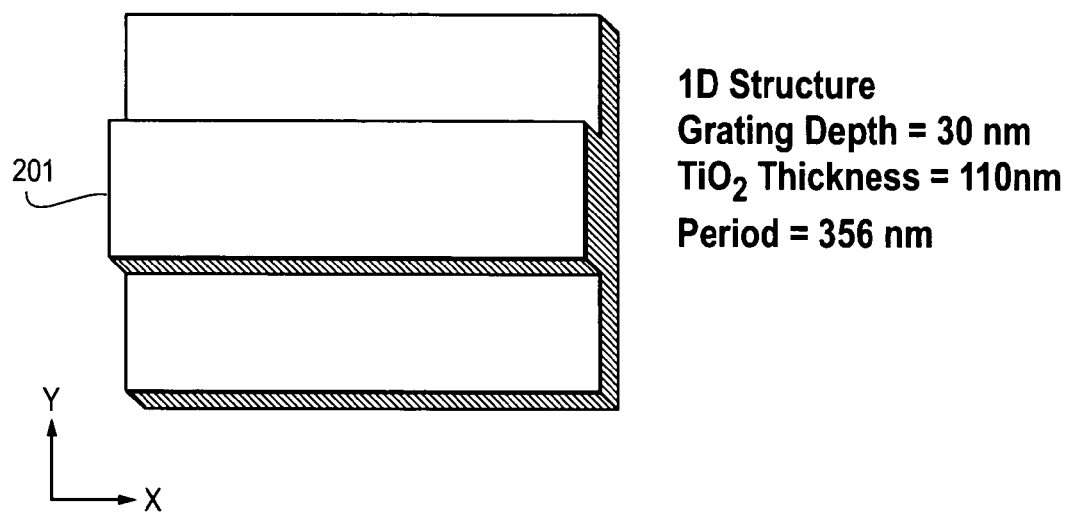
FIGS. 11A and 11B are perspective and cross-sectional views, respectively, of a one-dimensional linear grating structure designed solely for ER detection, modeled as a rough approximation of an ER chip disclosed in a prior art article of Budach et al.
Figure 11B:
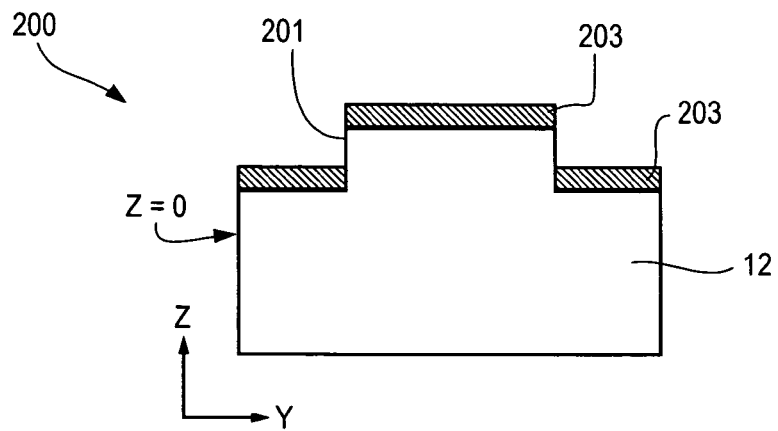

The simulations were done to determine the electromagnetic field distribution as well as reflection as a function of angle and wavelength for a representative device for ER enhancement of Cy5 dye. In particular, FIGS. 11A and 11B are perspective and cross-sectional views, respectively, of a one dimensional linear grating structure designed solely for ER detection. As shown, the structure has a linear grating profile consisting of a 30 nm raised ridge 201 and a 110 nm $TiO_2$ layer 203 covering the raised ridge 201. The periodicity is in the Y-direction (ridge 201 repeating every 356 nm.

Figure 12A:
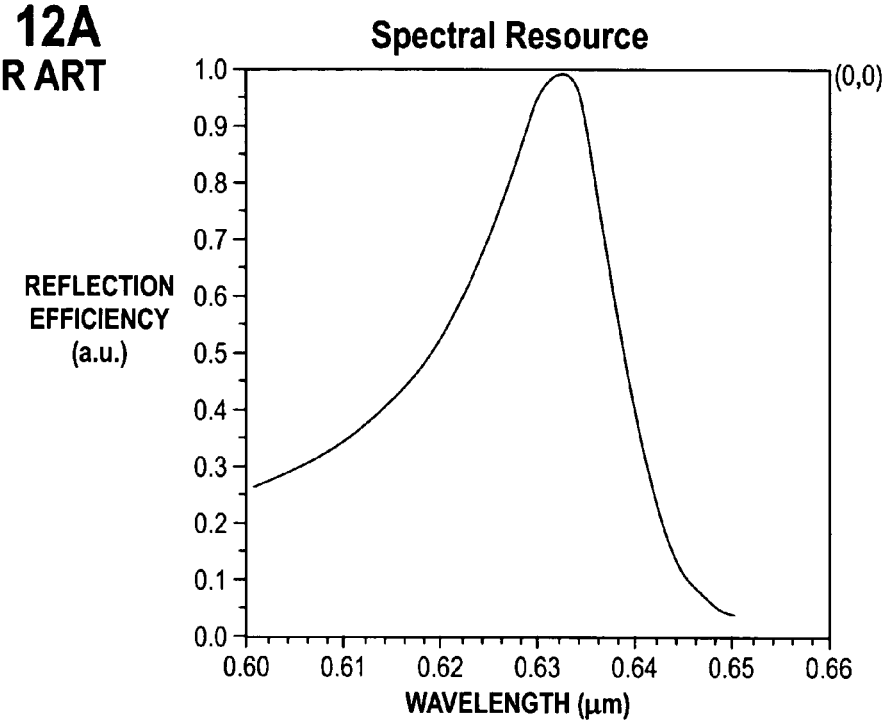
FIGS. 12A and 12B are graphs of the reflection efficiency as a function of wavelength and incidence angle, respectively, obtained when light polarized in the X direction is incident on the structure of FIGS. 11A and 11B.
Figure 12B:
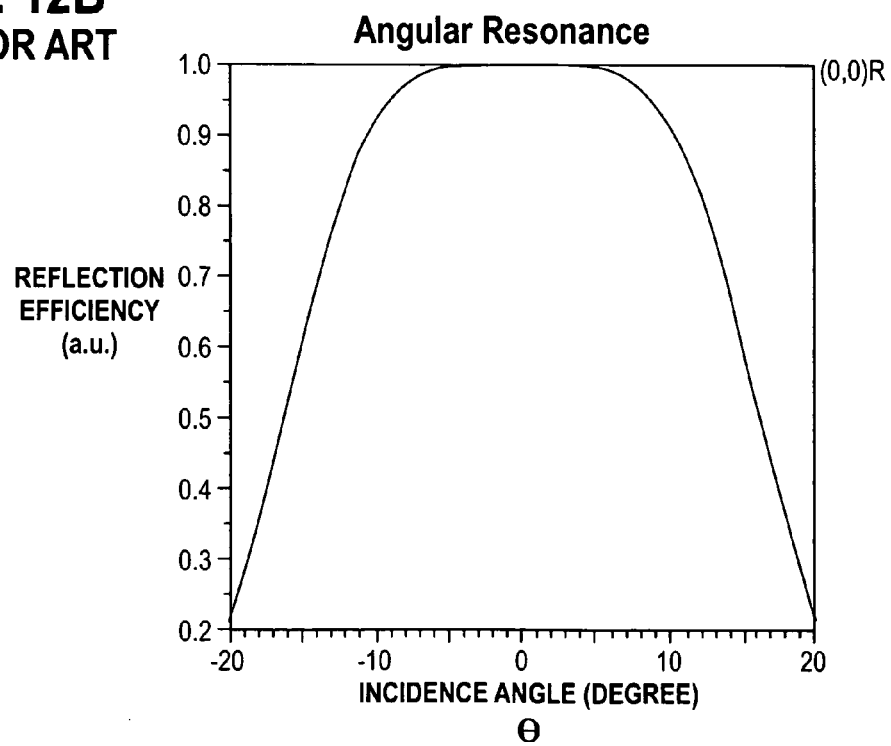

FIGS. 12A and 12B graphs the reflection efficiency as a function of wavelength and incidence angle, respectively, of the structure of FIGS. 11A and 11B, as determined by RCWA. Note that at normal incidence, the peak wavelength (632 nm in FIG. 12A) corresponds to the excitation wavelength of Cy5, and that there is a broad range of angles (FIG. 12B) with high reflection efficiency of the 632 nm wavelength when the incident light is rotated at an angle, theta, in a parallel direction with respect to the grating line or ridge 201.

Figure 13A:
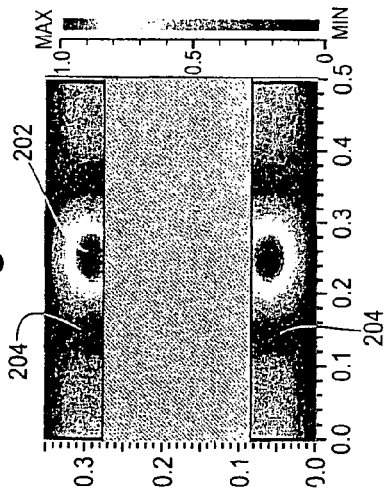
FIGS. 13A-13C are plots of the X, Y and Z components of electric field amplitude in the XY plane corresponding to the lower surface of the structure of FIGS. 11A and 11B located a Z=110 nm, for incident wavelength 632 nm.
Figure 13B:
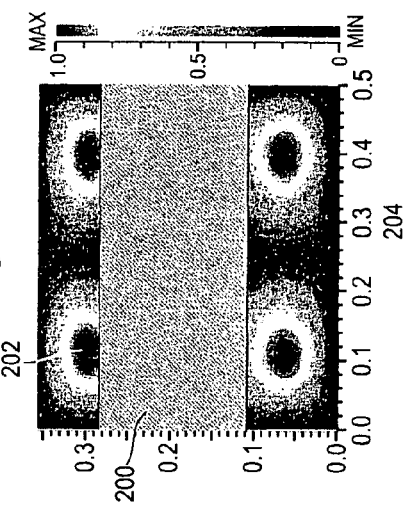
Figure 13C:
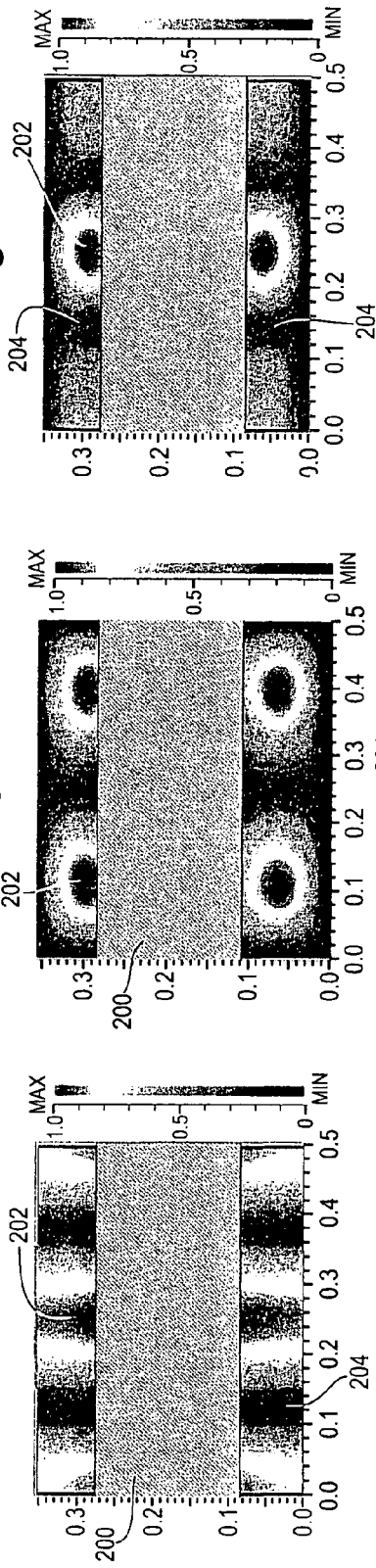
Figure 13D:
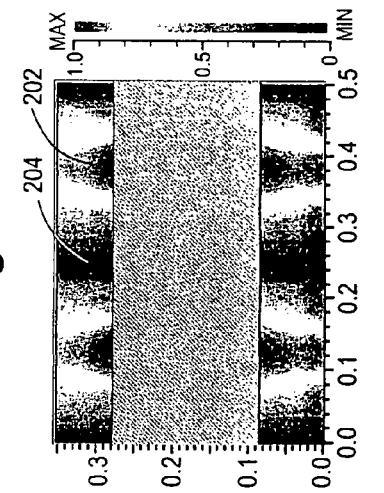
FIGS. 13D-13F plot of the X,Y and Z components of the magnetic field amplitude in the same XY plane represented in FIGS. 13A-13C for incident wavelength 632 nm.
Figure 13E:
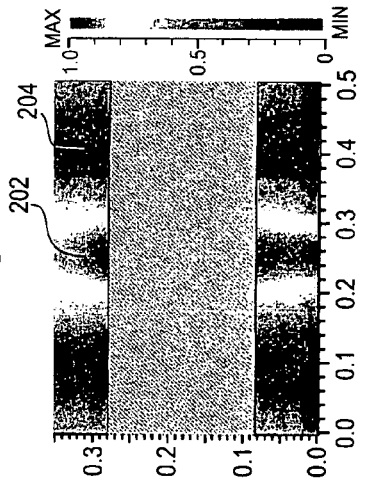
Figure 13F:
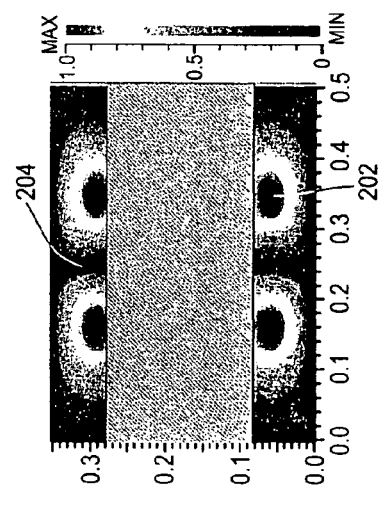

FIGS. 13A-13C are plots of the X, Y and Z components of electric field intensity in the XY plane corresponding to the lower surface of the structure of FIGS. 10A and 10B located a Z=110 nm, for incident wavelength at 632 nm. FIGS. 13D-13F plot of the X, Y and Z components of the magnetic field intensity in the same XY plane represented in FIGS. 13A-13C for incident wavelength at 632 nm.

The plots of FIG. 13 show the strength of the three components of the electric field vector (Ex, Ey, and Ez) and the magnetic field vector (Hx, Hy, and Hz) as a function of XY position on the lower exposed surface of the device. The upper exposed portion of the structure 200 is shaded here because the upper surface lies in a different horizontal plane than the lower surface. In the computer simulation, the sensor is illuminated with a light source having a 1 V/m magnitude electric field and a 1 A/m magnetic field at the resonance wavelength. Hence, field strength values greater than 1 represent concentration of field intensity at the sensor surface resulting from resonance. The power of the electromagnetic field is calculated by the cross product of E and H field components. The field power, at a given location on the structure's surface, specifies the energy available to excite fluorophores bound to the structure's surface. Higher power will, in theory, result in higher fluorescence emission. The plots show that the electric and magnetic fields, and thus the power, do not distribute evenly over the structure's surface, but instead locations exist with higher than average power (areas in red and orange in a color version of the drawing indicated at 202) and with lower than average power (areas in a color version of the drawing, areas in violet or blue, indicated at 204).

Figure 14A:
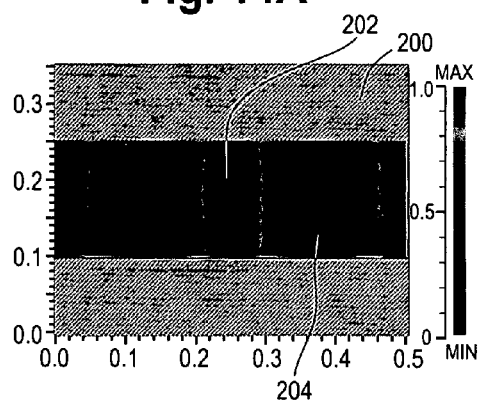
FIGS. 14A-14C are plots of the X, Y and Z components of electric field amplitude in the XY plane corresponding to the upper surface of the structure of FIGS. 11A and 11B located at Z=140 nm, for incident wavelength 632 nm.
Figure 14B:
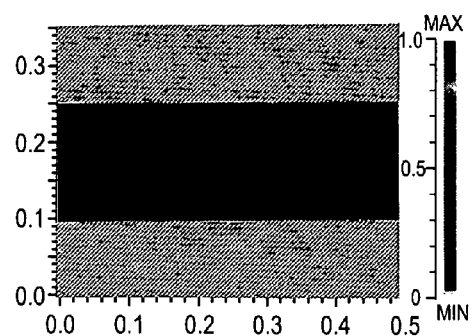
Figure 14C:
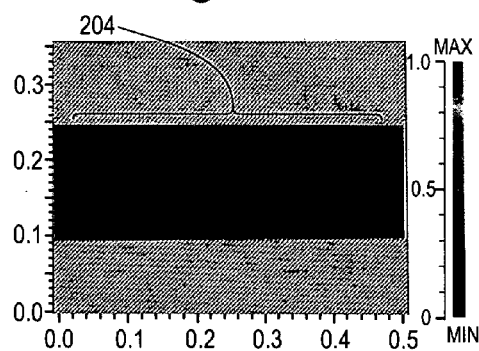
Figure 14D:
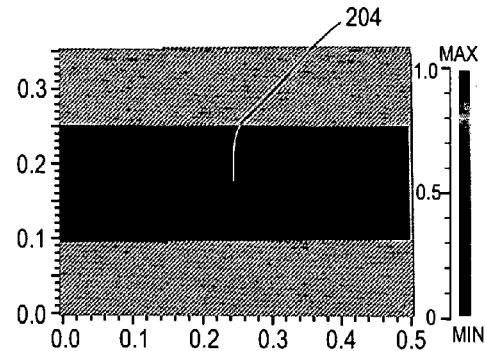
FIGS. 14D-14F plot the X,Y and Z components of the magnetic field amplitude in the same XY plane represented in FIGS. 14A-14C for incident wavelength 632 nm.
Figure 14E:
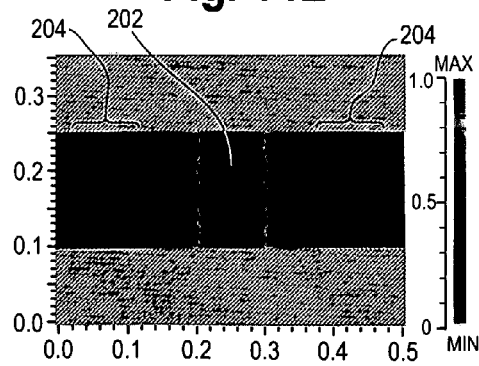
Figure 14F:
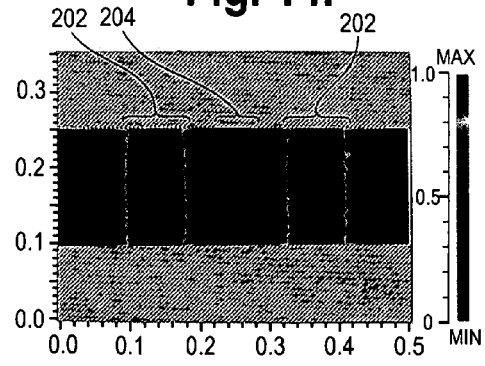

FIGS. 14A-14C are plots of the X, Y and Z components of electric field intensity in the XY plane corresponding to the upper surface of the structure of FIGS. 11A and 11B located at Z=140 nm, for incident wavelength 632 nm. FIGS. 14D-14F plot the X, Y and Z components of the magnetic field intensity in the same XY plane represented in FIGS. 14A-14C for incident wavelength 632 nm.

These plots (FIG. 14) show the strength of the three components of the electric field vector (Ex, Ey, and Ez) and the magnetic field vector (Hx, Hy, and Hz) as a function of XY position on the upper exposed surface of the device. The lower exposed portion of the structure is shaded here as indicated at 200 because the upper surface lies in a different horizontal plane than the lower surface. As with the plots of FIG. 13, in the simulation the sensor is illuminated with a light source having 1 V/m electric field, 1 A/m magnetic field amplitudes at the resonant wavelength. Hence, field strength values greater than 1 represent the concentration of field intensity at the sensor surface, resulting from resonance. The cross products of E and H field components, as before, represent the instantaneous power distribution, at the resonant wavelength, available for fluorophore excitation.

A. Holes Embodiment Example

Now, a specific example of a 2D "holes" embodiment of a combined biosensor will be described in conjunction with FIGS. 15-19. The biosensor is constructed in two dimensions so as to be optimized for both ER and label-free (BIND) detection using a single device.

Figure 15A:
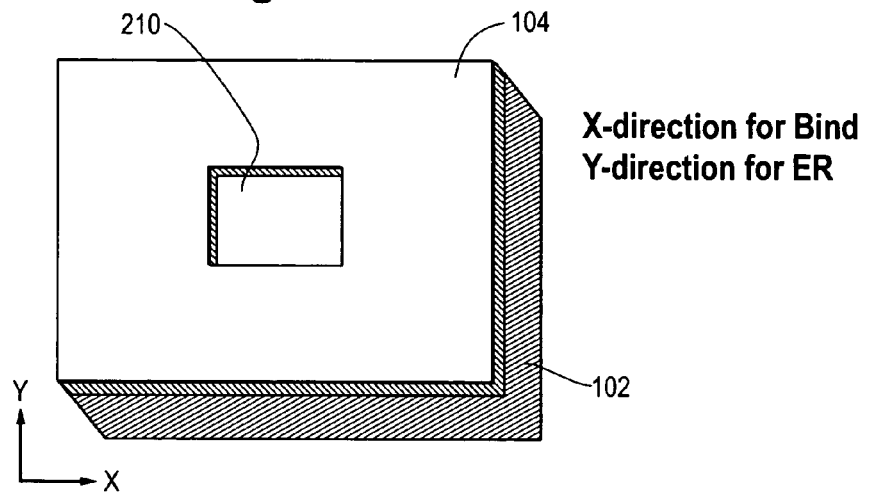
FIGS. 15A and 15B are perspective and cross-sectional views, respectively, of a two-dimensional grating design characterized by periodic holes in a grating structure which is optimized for BIND (label-free) detection in a water environment when illuminated by X polarized light and optimized for ER detection in an air environment when illuminated by Y polarized light.
Figure 15B:
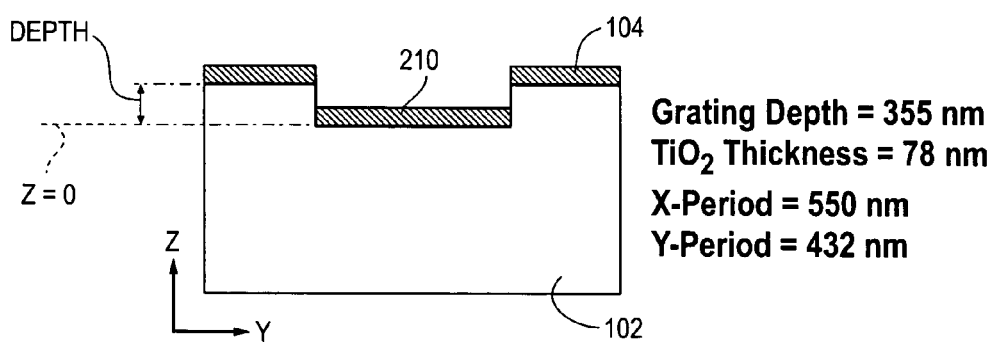

FIGS. 15A and 15B provide perspective and cross-sectional views, respectively, of a unit cell for a two-dimensional grating design characterized by periodic holes 210 in a grating structure. The grating design optimizes for water mode BIND (label-free) detection and air mode ER detection. The device includes an upper $TiO_2$ layer 104 of 78 nm thickness and a lower substrate 102 layer of UV-cured material having a grating pattern as shown applied to a base substrate sheet.

The two-dimensional unit cell shown in FIGS. 15A and 15B differentiates from the one-dimensional linear grating design of FIGS. 11A and 11B. The structure of FIGS. 15A and 15B is designed in such a way that incident light polarized perpendicular to the X-axis, as shown, produces a BIND signal, incident light polarized perpendicular to the Y-axis enables ER measurement. Using this design method, the BIND and ER resonant wavelengths (at a particular angle of incidence—preferably near normal incidence) may be chosen independently, and so the respective BIND and ER resonant wavelengths may occur at very different values. The combined BIND/ER structure described in this embodiment is optimized to provide a BIND resonance in the near infrared (~800-900 nm) wavelength region, while providing an ER resonance at 632.5 nm for excitation of the Cy5 fluorophore. In this example, the design assumes a water environment over the sensor during BIND measurement and an air environment over the sensor during ER measurement. The differing wavelength requirements for ER and BIND engender selection of a unit cell with a rectangular "hole" (210). Thus, the unit cell may have differing dimensions in the X and Y directions. For example, the period in the X direction is 550 nm for the BIND wavelength, but is 432 nm in the Y direction as required for the lower wavelength ER resonance. The fabrication process dictates that the high refractive index dielectric thickness will be the same in the X and Y directions. For fabrication simplicity, the design also has uniform grating depth. The fabrication process will also result in rounding of the hole corners, however the principal function of the design remains unchanged. One skilled in the art will appreciate that when a computer is used to generate and test a design such as shown in FIGS. 15A and 15B, the designer can change the specific dimensions of the unit cell, grating depth, and coating layers and run simulations of field intensity, peak wavelength, reflectance as a function of theta, and other tests and may select other dimensions while still achieving acceptable results. Thus, the example of FIGS. 15A and 15B is meant to be an illustrative embodiment and not limiting in scope.

Figure 16:
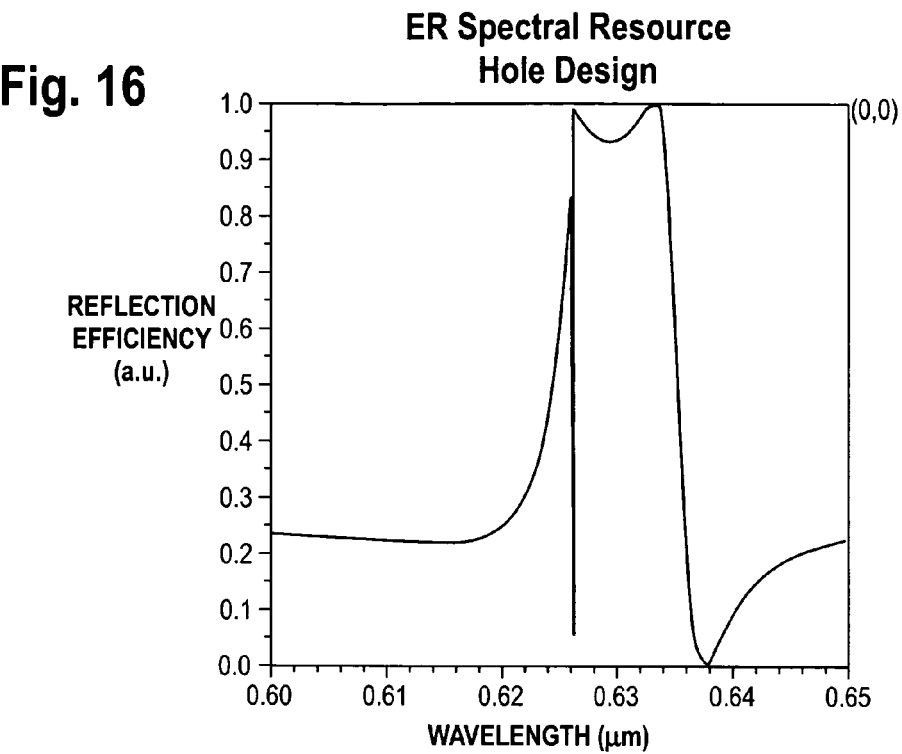
FIGS. 16 and 17 are graphs of the reflection efficiency as a function of wavelength and incidence angle (632.5 nm), respectively, obtained when light polarized in the Y direction is incident on the structure of FIGS. 15A and 15B. These figures demonstrate utility in the ER mode.
Figure 17:
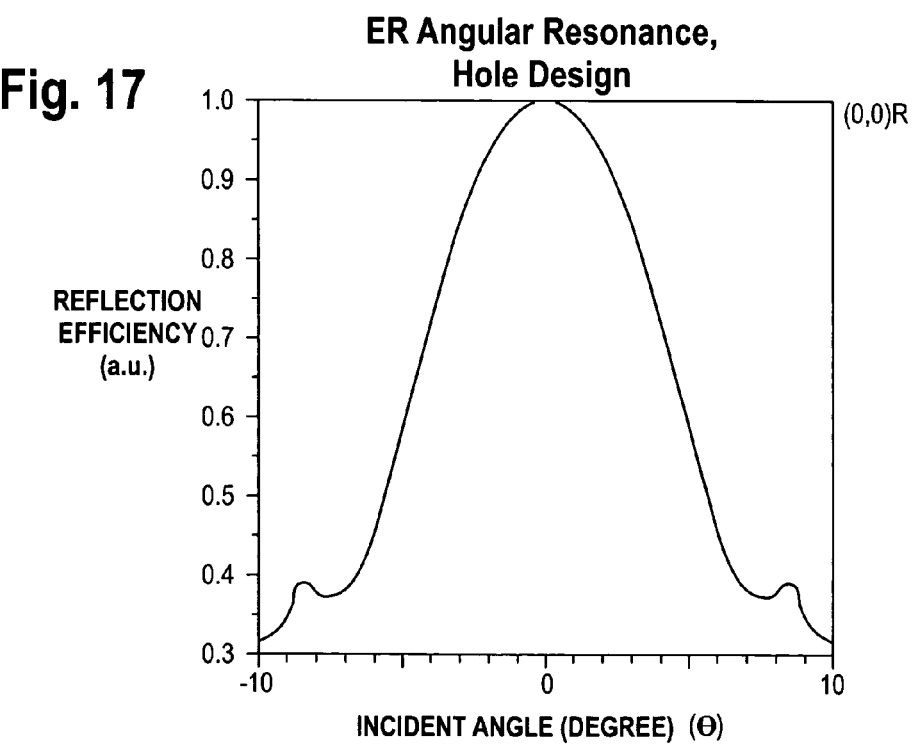

FIGS. 16 and 17 are graphs of the reflection efficiency as a function of wavelength and incidence angle, respectively, for the structures disclosed in FIGS. 15A and 15B when illuminated with light polarized along the Y axis. These figures, generated by RCWA, represent operation in an ER mode. FIG. 17 shows that, at the resonant wavelength, the reflected intensity as a function of incident angle observes the acceptance angle for light that will induce a significant ER effect. In physical measurements, the double peak and dip between the peaks in the plot of FIG. 16 may not resolve.

Figure 18A:
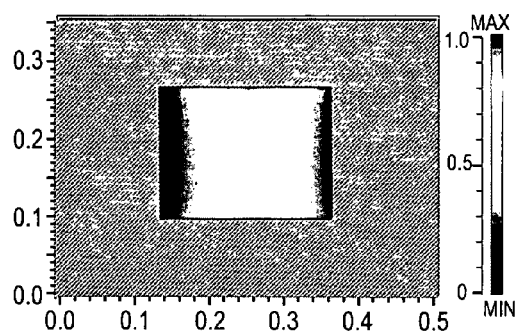
FIGS. 18A-18C are plots of the X, Y and Z components of electric field amplitude in the XY plane corresponding to the lower surface of the structure of FIGS. 15A and 15B at Z=78 nm, for incident wavelength 632.5 nm.
Figure 18B:
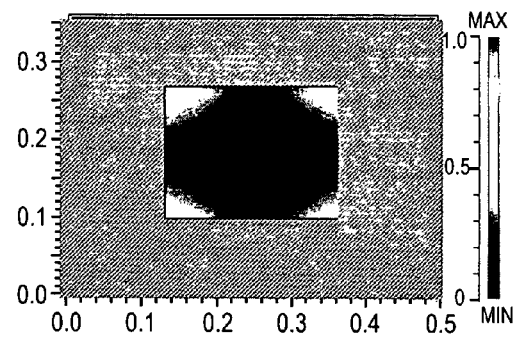
Figure 18C:
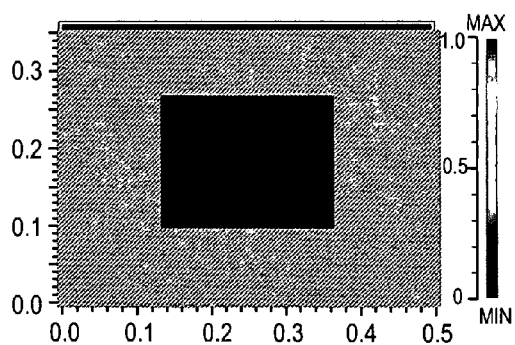
Figure 18D:
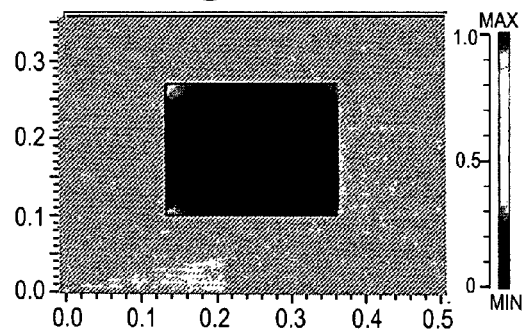
FIGS. 18D-18F plot the X,Y and Z components of the magnetic field amplitude in the same XY plane represented in FIGS. 18A-18C for incident wavelength 632.5 nm.
Figure 18E:
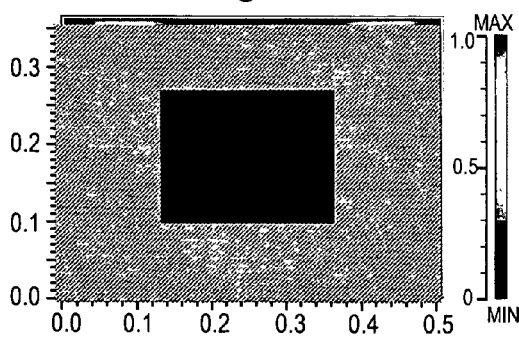
Figure 18F:
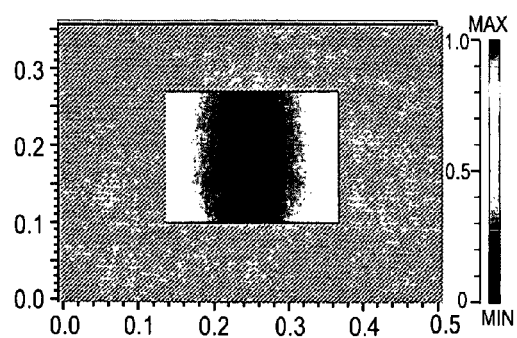

In a similar manner to the 1D example above, RCWA calculations may be used to determine the spatial distribution of the amplitude of the electric field magnitude components (Ex, Ey, and Ez) and the magnetic field components (Hx, Hy, Hz) at the ER resonant wavelength for the structure illustrated in FIGS. 15A and 15B. FIGS. 18A-18C plots the X, Y and Z components of electric field intensity in the XY plane corresponding to the lower surface of the structure of FIGS. 15A and 15B at Z=78 nm, for incident wavelength 632.5 nm. FIGS. 18D-18F plot the X,Y and Z components of the magnetic field intensity in the same XY plane represented in FIGS. 18A-18C for incident wavelength 632.5 nm. These field amplitude distributions are shown for the lower $TiO_2$ surface inside the hole for a single unit cell that repeats in both the X and Y directions. As before, the cross product of the E and H field components describes the instantaneous power density distribution responsible for fluorescent excitation at the lower surface. A 1 V/m electric field, 1 A/m magnetic field plane wave at the resonant wavelength is used as the illumination source.

Figure 19A:
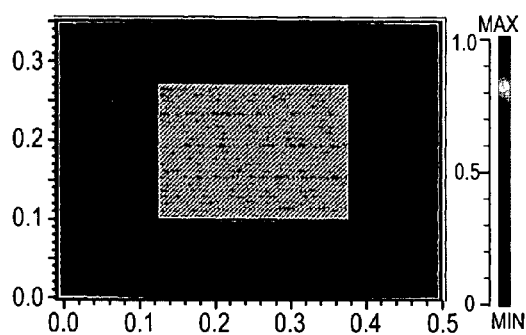
FIGS. 19A-19C are plots of the X, Y and Z components of the electric field amplitude in the XY plane corresponding to the upper surface of the structure of FIGS. 15A and 15B at Z=433 nm for incident wavelength 632.5 nm.
Figure 19B:
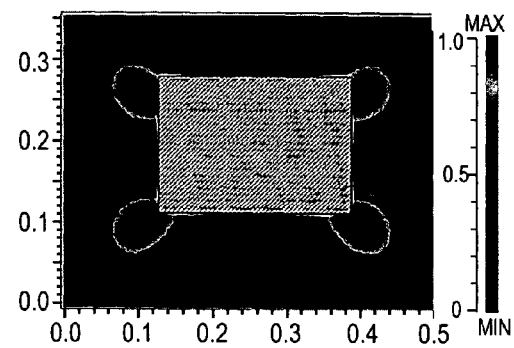
Figure 19C:
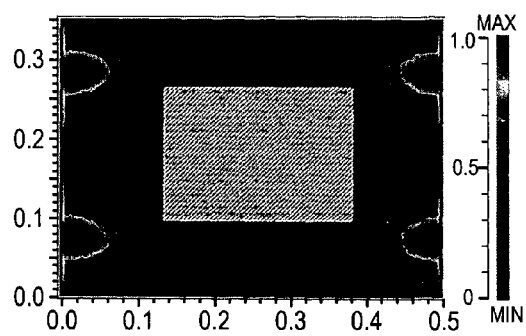
Figure 19D:
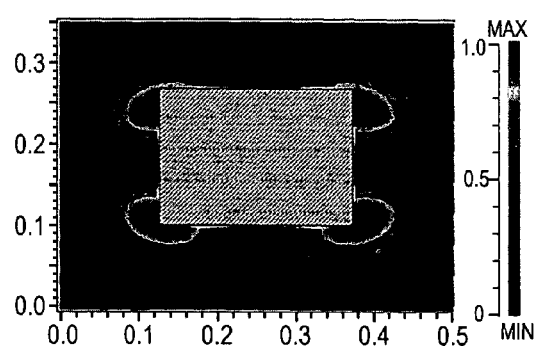
FIGS. 19D-19F are plots of X,Y and Z components of the magnetic field amplitude in the same XY plane represented in FIGS. 19A-19C for incident wavelength 632 nm.
Figure 19E:
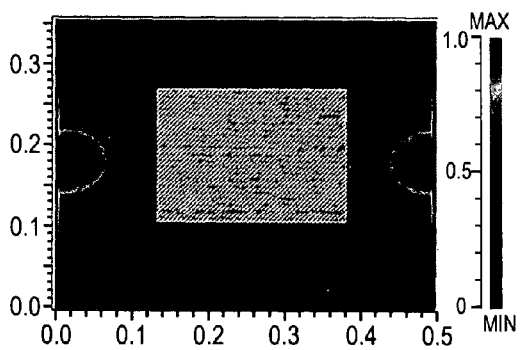
Figure 19F:
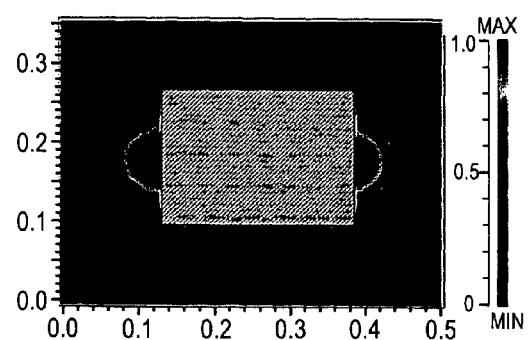

Similarly, the electromagnetic field distributions may be computed for the upper $TiO_2$ surface of the unit cell. FIGS. 19A-19C plots the X, Y and Z components of the electric field amplitude in the XY plane corresponding to the upper surface of the structure of FIGS. 15A and 15B at Z=433 nm for incident wavelength 632.5 nm. FIGS. 19D-19F plot of X,Y and Z components of the magnetic field amplitude in the same XY plane represented in FIGS. 19A-19C for incident wavelength 632 nm. Note that the maximum amplitude of each field component, as indicated by the plot legend, is substantially higher than those of the prior art design indicating that higher power density may be obtained at the surface of this device. In particular, note that a substantial Ez component has appeared in contrast to the Ez amplitude of the 1D prior design.

Figure 19G:
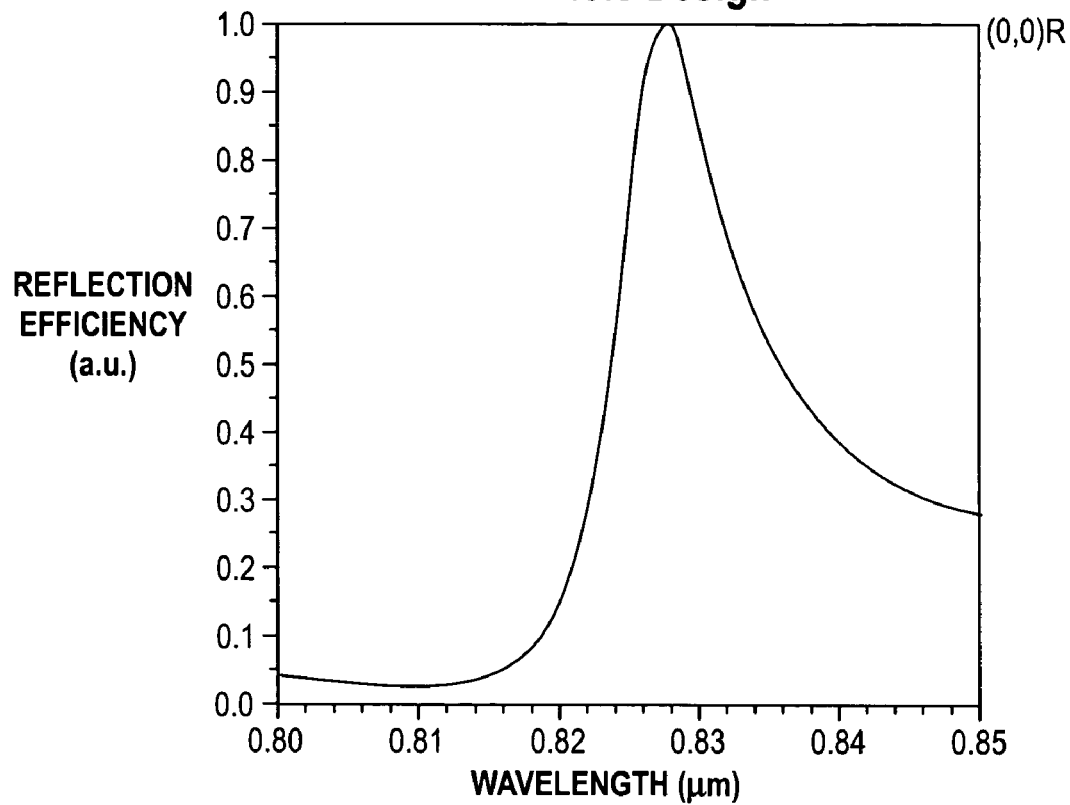
FIG. 19G is a graph of reflection efficiency as a function of wavelength for the embodiment of FIG. 15 obtained when illuminated by light polarized in the X direction. This resonance peak is used for label-free detection.

FIG. 19G plots reflection efficiency as a function of wavelength modeled using incident illumination polarized parallel to the X axis. Light with X axis polarization, incident on the design represented by FIG. 15, generates a resonance useful for label-free detection, with a width of approximately 12.5 nm and a maximum near 830 nm. The simulation can also predict the bulk refractive index shift coefficient, defined as delta (PWV)/delta(n), where delta (PWV) is the shift in the peak wavelength value induced by a refractive index change of delta (n) in the environment above the sensor. This quantity indicates the sensitivity of the sensor to binding of a sample to the grating surface. The "Hole" design described by FIGS. 15A and 15B has a predicted bulk shift coefficient of 200, indicating that the structure will provide sensitive label-free performance.

B. Posts Embodiment Example

A 2-dimensional grating structure using a repeating unit cell characterized by a post will now be described with reference to FIGS. 20-24.

Figure 20A:
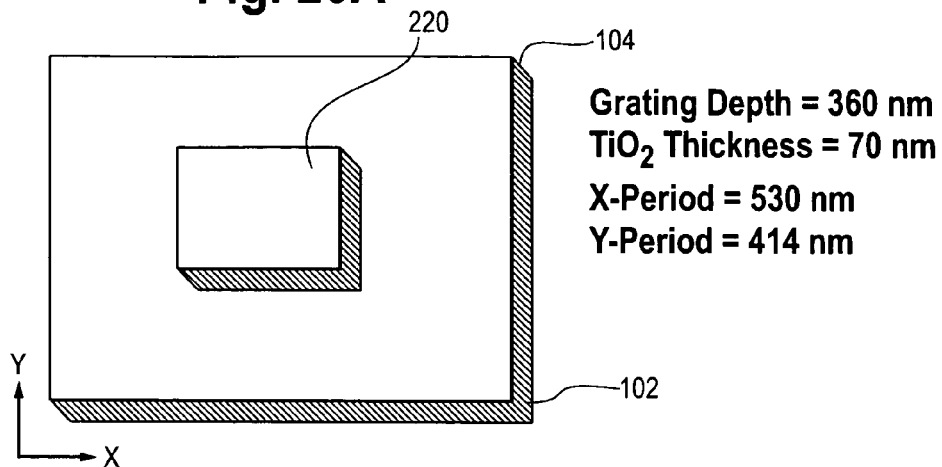
FIGS. 20A and 20B show perspective and cross-sectional views, respectively, of a two-dimensional grating design characterized by periodic posts in a grating structure which is optimized in one direction for BIND (label-free) detection in a water environment when illuminated by X polarized light and optimized for ER detection in an air environment when illuminated by Y polarized light.
Figure 20B:
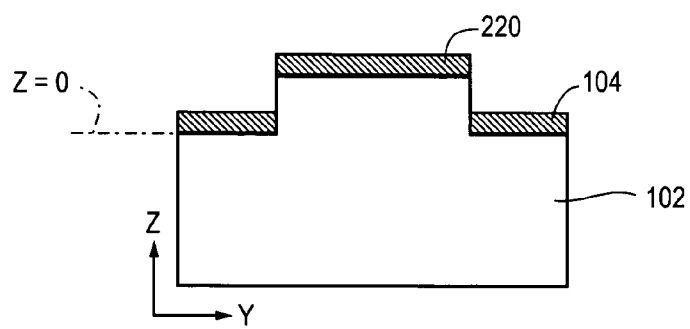

FIGS. 20A and 20B are perspective and cross-sectional views, respectively, of a unit cell of 2-dimensional grating design characterized by periodic posts 220 formed in the sensor surface. Each unit cell has one post 220. The posts 220 are raised projections in a substrate material 102 (e.g., UV cured polymer) which is applied to a base sheet (not shown). A high index of refraction (e.g., $TiO_2$) coating is applied to the projections and substrate as shown in the Figures. The structure is optimized for BIND (label-free) detection in a water environment using light polarized in the X direction and optimized for ER detection in an air mode, using light polarized in the Y direction.

The design of FIG. 20 was studied by RCWA computer simulation. While the previous structure unit cell of FIG. 15 contained a "hole" region surrounded by regions at a higher plane in the z-direction, the grating structure of FIG. 20 contains a central "post" region, surrounded by regions at a lower plane in the z-direction. As before, the design of FIG. 20 represents a BIND/ER combined structure that is optimized to provide a BIND resonance in the near infrared (~800-900 nm) wavelength region, while providing an ER at 632 nm for excitation of the Cy5 fluorophore. In this example, the design again assumes a water environment over the sensor during BIND measurement and an air environment over the sensor during ER measurement. These differing wavelength requirements for ER and BIND, engender selection of a rectangular "post" unit cell. Thus, the unit cell may have differing dimensions in the X and Y directions. For example, the period in the X direction is 530 nm for the BIND wavelength, but is 414 nm in the Y direction as required for the lower wavelength ER resonance. The fabrication process again dictates that the high refractive index dielectric thickness will be the same in the X and Y directions. For fabrication simplicity, the design also has uniform grating depth. The fabrication process will also result in rounding of the post corners, however the principal function of the design remains unchanged. The example of FIG. 20 is meant as an illustrative example not limiting in scope. The specific dimensions can of course vary.

Figure 21A:
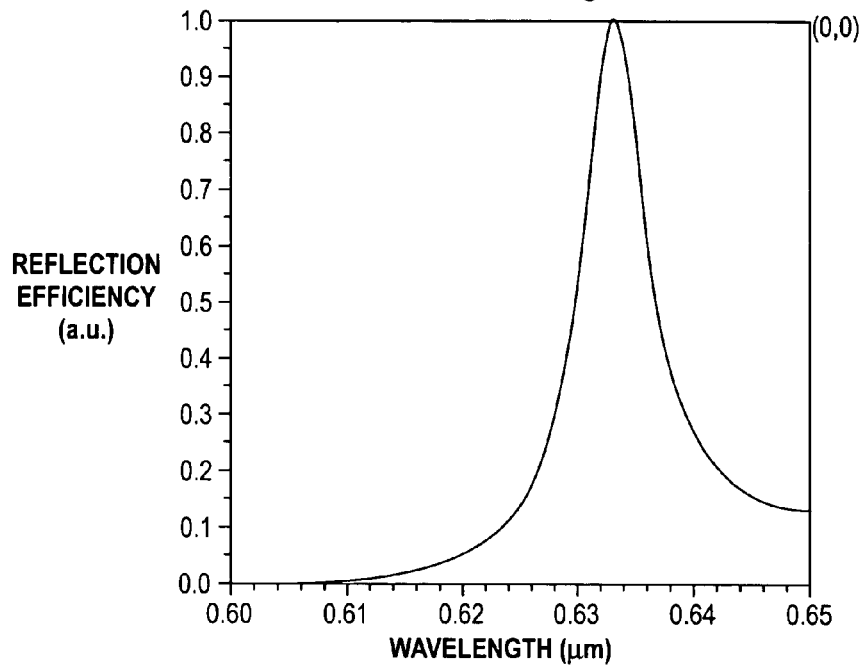
FIGS. 21A and 21B graph the reflection efficiency as a function of wavelength and incidence angle (633 nm wavelength), respectively, when light polarized in the X direction is incident on the structure of FIGS. 20A and 20B. The figures demonstrate utility in the ER mode.
Figure 21B:
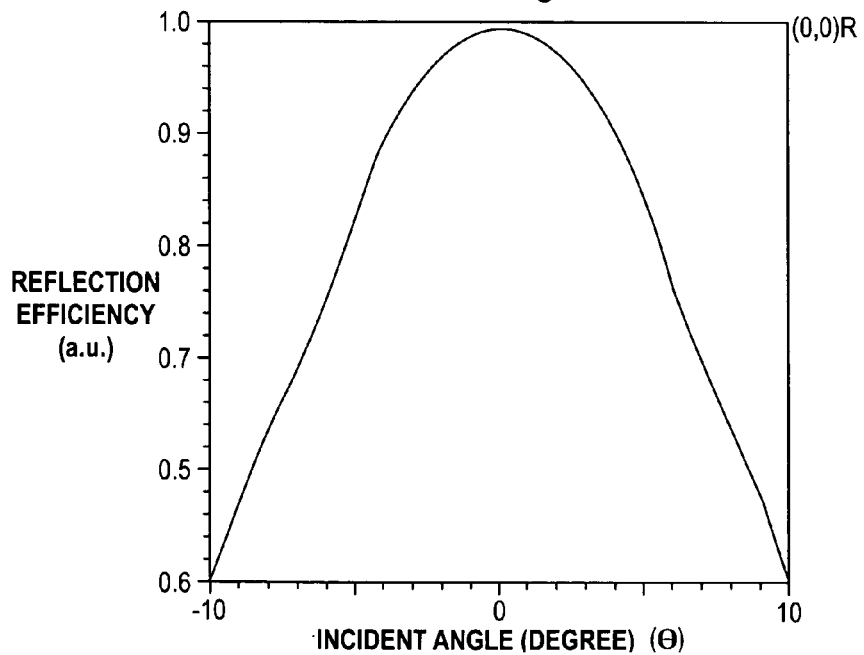

FIGS. 21A and 21B graph the reflection efficiency as a function of wavelength and incidence angle, respectively, for the structures represented by FIGS. 20A and 20B when illuminated with light polarized along the Y axis. These figures, generated by RCWA, represent operation in an ER mode. FIG. 21A shows a resonance peak maximum reflection at 633 nm and FIG. 21B shows a resonance across a range of incident angles when illuminated at 633 nm.

Figure 22A:
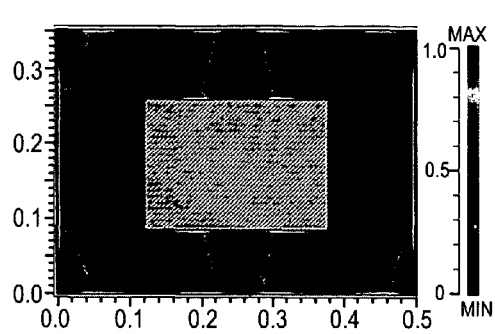
FIGS. 22A-22C are plots of the X, Y and Z components of electric field amplitude in the XY plane corresponding to the lower surface of the structure of FIGS. 20A and 20B at Z=70 nm, for incident wavelength 633 nm.
Figure 22B:
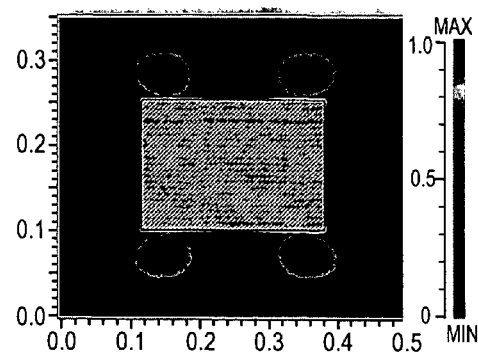
Figure 22C:
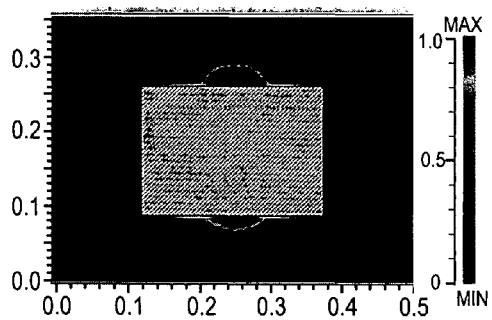
Figure 22D:
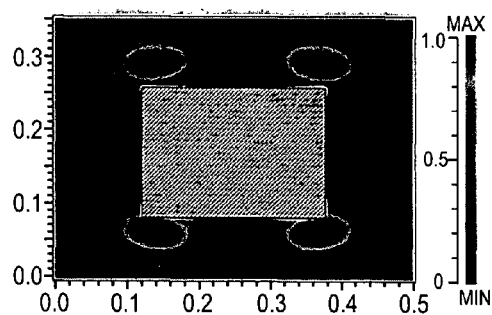
FIGS. 22D-22F plot the X,Y and Z components of the magnetic field amplitude in the same XY plane represented in FIGS. 22A-22C for incident wavelength 633 nm.
Figure 22E:
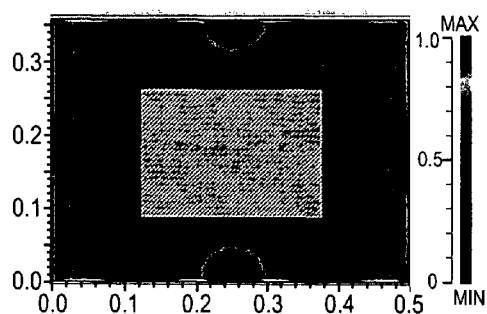
Figure 22F:
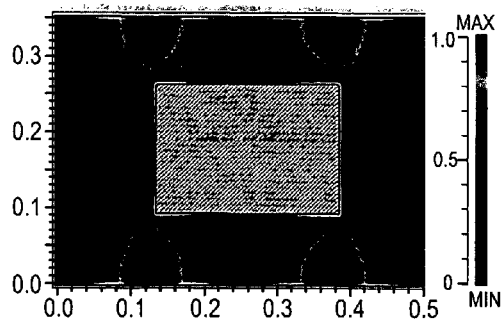

The RCWA computer simulations may be used to determine the spatial distribution of the amplitude of the electric field components (Ex, Ey, and Ez) and the magnetic field components (Hx, Hy, Hz) at the ER resonant wavelength. FIGS. 22A-22C plot the X, Y and Z components of electric field amplitude in the XY plane corresponding to the lower surface of the structure of FIGS. 20A and 20B at Z=70 nm, for incident wavelength 633 nm. FIGS. 22D-22F plot the X,Y and Z components of the magnetic field amplitude in the same XY plane represented in FIGS. 22A-22C for incident wavelength 633 nm. As shown in FIG. 22, the field amplitude distributions are shown for the lower surfaces surrounding the posts for a single unit cell that repeats in the X and Y directions. As before, the cross product of the E and H field components describes the instantaneous power density distribution responsible for fluorescent excitation at the lower surface. A 1 V/m electric field, 1 A/m magnetic field plane wave at the resonant wavelength again serves as the illumination source.

Figure 23A:
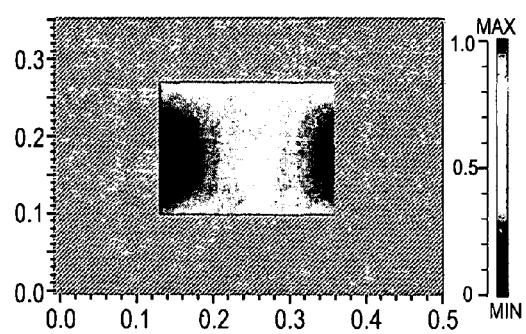
FIGS. 23A-23C plot the X, Y and Z components of the electric field amplitude corresponding to the upper surface of the structure of FIGS. 20A and 20B at Z=430 nm for incident wavelength 633 nm.
Figure 23B:
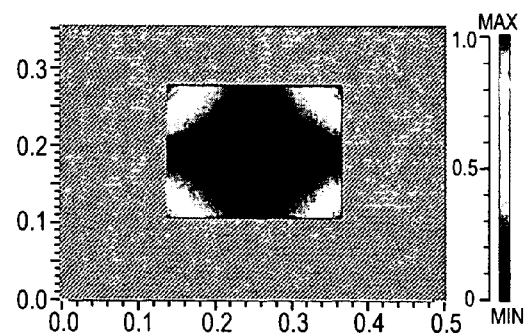
Figure 23C:
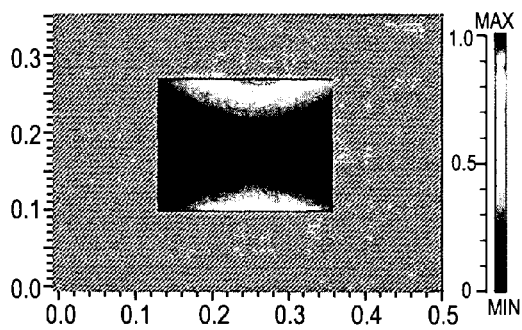
Figure 23D:
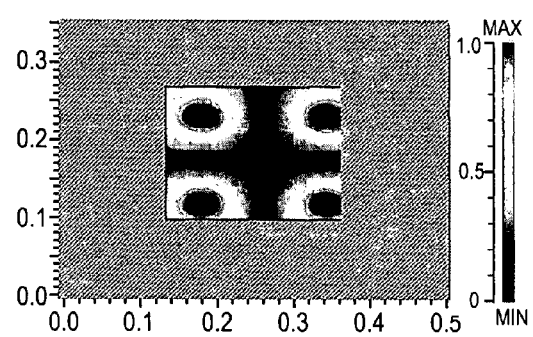
FIGS. 23D-23F plot the X, Y and Z components of the magnetic field amplitude, in the same XY plane represented by FIGS. 23A-C for incident wavelength 632 nm.
Figure 23E:
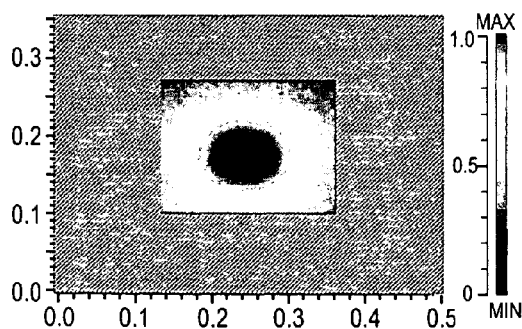
Figure 23F:
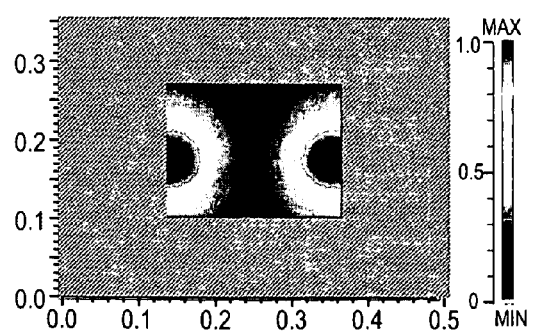

Similarly, the electromagnetic field distributions may be computed for the upper $TiO_2$ surfaces of the unit cell. FIGS. 23A-23C plot the X, Y and Z components of the electric field amplitude corresponding to the upper surface of the structure of FIGS. 20A and 20B at Z=430 nm for incident wavelength 633 nm. FIGS. 23D-23F plot the X,Y and Z components of the magnetic field amplitude in the same XY plane represented by FIGS. 23A-C for incident wavelength 632 nm. Note that the maximum magnitude of the fields is again substantially higher than the prior art design (FIG. 10) for each of the field components, indicating that potentially higher power density may be obtained at the surface of this device.

Figure 24:
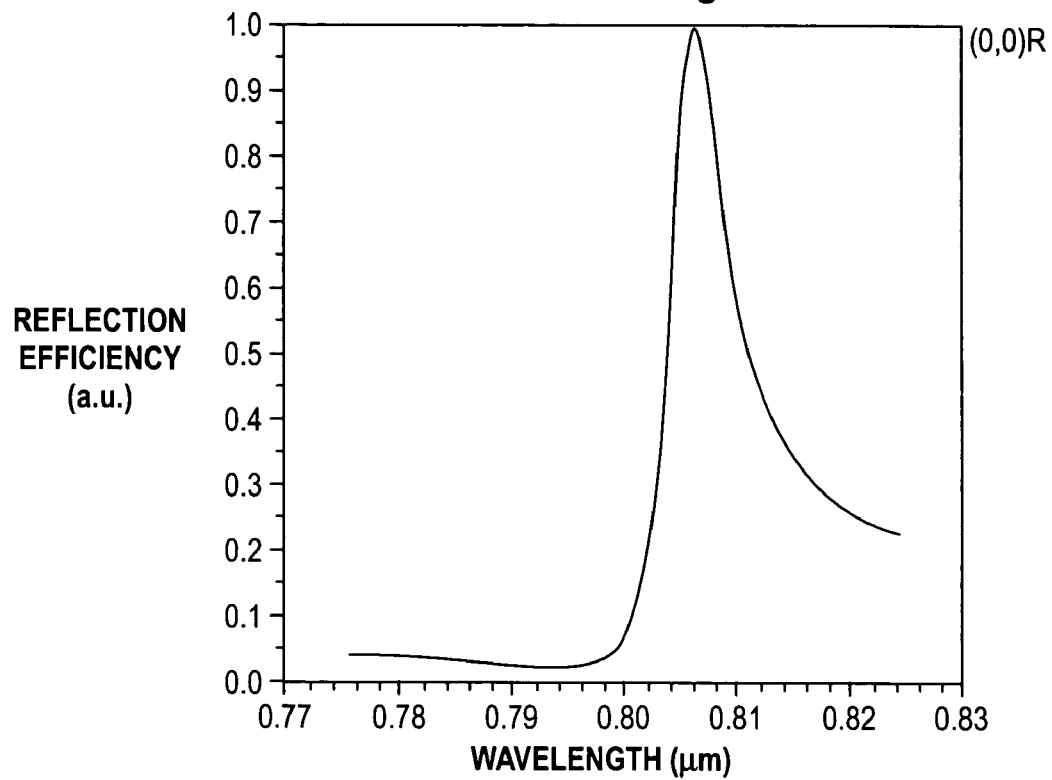
FIG. 24 is a graph of reflection efficiency as a function of wavelength for the embodiment of FIG. 20 obtained when illuminated by light polarized in the X direction. This resonance peak is used for label-free detection.

FIG. 24 plots reflection efficiency modeled using incident illumination polarized parallel to the X axis. Light with X-axis polarization, incident on the deign represented by FIG. 15, generates a resonance useful for label-free detection, with a width of approximately 8 nm and reflectance maximum near 805 nm. The simulations produce a shift coefficient (explained above) of 90. The embodiment of FIG. 20 is also expected to provide sensitive label-free performance, though probably lower than the embodiment of FIG. 15. Comparison of amplitude values and shift coefficients between the two 2D designs suggests that further optimization of the grating structure could emphasize the performance of one detection mode as a tradeoff for reduced performance in the other detection mode.

The amount of amplification for ER detection relates to the power transferred from the device structure to a distribution of fluorophores on the sensor surface within at the excitation wavelength range of the fluorophore. The power density distribution of the sensor surface at the resonant wavelength, provided that the resonant wavelength falls within the excitation wavelength range, therefore provides a means for comparing the sensitivity of different ER device designs. One can define the cross product E (max)×H (max) as a field power or "magnification factor". While a more thorough analysis of the intensity distribution of the evanescent field from the tops, bottoms, and sides of the structure, and a detailed integration of power density to account for differences between higher and lower power regions would provide a more exact prediction of whether one device will function more effectively than another, the product of the maximum amplitude of an E component with an orthogonal H component provides a very simple, rough way of comparing designs. Using RCWA analysis for the exposed upper and lower planes of the devices, the E×H magnification factor for the prior art design of FIGS. 11A and 11B is 144. Conversely, for the "holes" unit cell design of FIGS. 15A and 15B, the E×H magnification factor is 6217, while for the "posts" design of FIGS. 20A and 20B, the E×H magnification factor is 5180. Based on this rough analysis, the ER aspects of the 2D grating designs of FIGS. 15 and 20 appear to provide the potential for higher sensitivity ER performance than the linear grating design of FIG. 10. Moreover, the designs of FIGS. 15 and 20 are expected, based on the computer simulations, to provide excellent sensitivity for label-free detection, as explained above. Therefore, useful combined ER and label-free detection in a single device is achieved in the above-described 2D grating embodiments.

C. Two-Level, 2-D Gratings

Figure 28A:
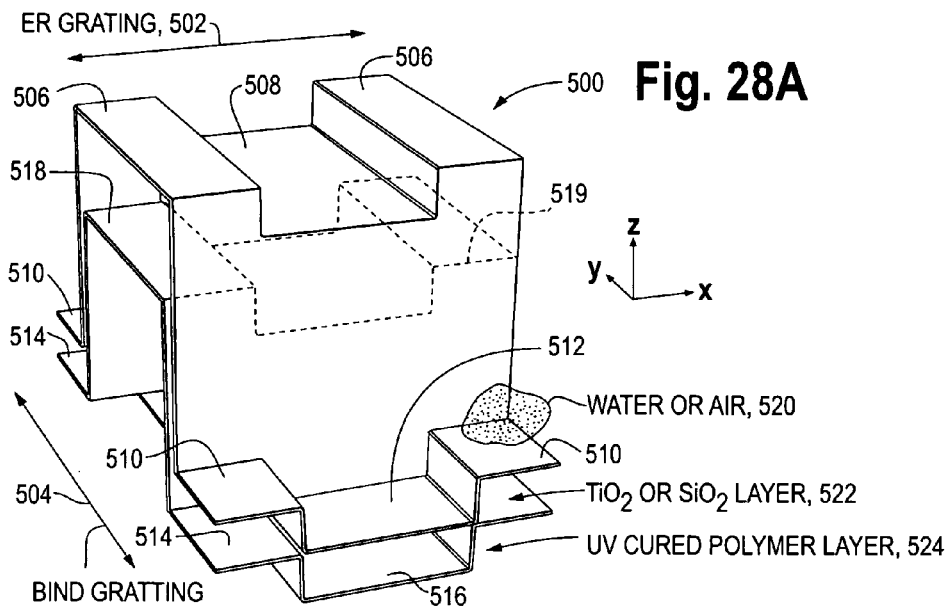
FIGS. 28A-C are three views of a unit cell showing a two-level, two-dimensional grating structure for yet another embodiment of a combined ER and label-free sensor.
Figure 28B:
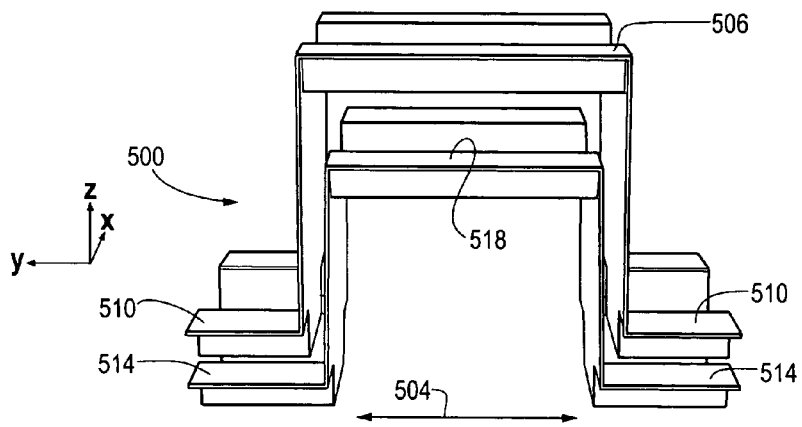
Figure 28C:
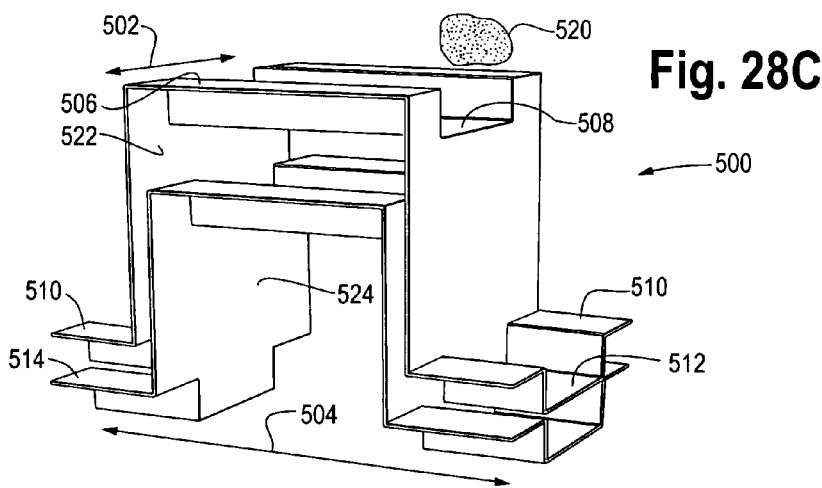
Figure 29:
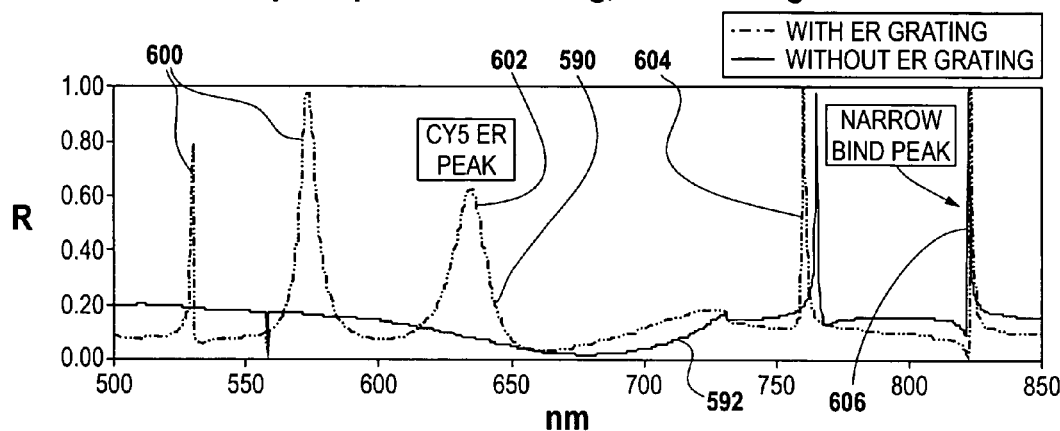
FIG. 29 is a graph of the reflection spectrum (relative intensity as a function of reflected light wavelength) obtained using a computer simulation of the structure of FIGS. 28A-C.

FIGS. 28A-C are three perspective views of yet another embodiment of a unit cell 500 for a biosensor grating structure constructed and designed for a combined ER and label-free (BIND) detection. In order to appreciate some of the features of this structure, it will be useful to recapitulate on the design aspects pertinent to evanescent resonance (ER) and label-free (BIND) sensors. Such sensors differ in three basic design aspects, namely: resonance wavelength, resonance width, and grating depth.

Resonance Wavelength

The ER sensor prefers resonance to occur in within a few (~+/−2) nm of the excitation wavelength. Given that the excitation light generally comes from a laser and has very narrow bandwidth, this requirement places high specificity on the wavelength location of the ER resonance. The BIND mode of operation does not have this limitation and may benefit from a resonance at another wavelength e.g. outside ambient lighting wavelength range or to separate the BIND signal spectrally from the ER excitation source thereby eliminating potential overlapping detection conflicts.

Resonance Width

The ER sensor must have a resonance wide enough for it to overlap the excitation wavelength in the presence of variables such as biological coating thickness and illumination numerical aperture. In practice, the ER resonance should not have a full width at half maximum (FWHM) less than about 5 nm, and more preferably between 10 and 15 nm. On the other hand, BIND sensitivity increases approximately as 1/sqrt (FWHM) because peak location uncertainty decreases as the peak width narrows.

Grating Depth

BIND sensors give greater resonance wavelength shift when more biological material adheres to the grating. A deeper grating offers more surface area for binding biological material. The ER effect does not necessarily improve and may degrade as the ER grating depth increases.

The 2-D designs described previously have uniform grating depth (e.g. in the post examples the height of the posts, or in the holes example the depth of the holes). Selecting a single grating depth may involve a compromise between BIND and ER performance both in terms of peak width and surface area, i.e. BIND PWV shift.

The design of the biosensor of FIGS. 28A-C is a two-level, two-dimensional design. The specifics of the design will be discussed below in greater detail. This design maintains a narrow TM BIND resonance and high BIND shift performance, while simultaneous providing a wider TE ER resonance. Similar to previously described two-dimensional designs, the BIND and ER gratings can have different periods and hence independently determined resonance wavelengths.

This "two level" "comBIND" design of FIGS. 28A-C comprises a multitude of repeating unit cells 500, each of which superimposes a relatively shallow ER grating 502 extending in the X direction on a relatively deep BIND grating 504, extending in the Y direction. FIGS. 28A-29C depict one "unit cell" 500 for this design, which, when replicated in the XY plane forms the complete grating.

The unit cell 500 consists of a UV-cured polymer layer 524 which is applied using a master grating wafer to a base substrate sheet such as PET film (not shown). The polymer layer 524 has the structure of the BIND grating 504, namely alternating low and high regions extending in the Y direction. In the X direction, the grating also has alternating low and high regions, although the relative height of the high region compared to the low regions of the UV-cured polymer layer 524 in the X direction is much less than in the Y direction.

A $TiO_2$ (or alternatively $SiO_2$ or $Ta_2O_5$) layer 522 is deposited over the UV-cured polymer layer. This layer has uniform thickness in the illustrated embodiment. The layer 522 includes upper repeating surface 506, 508, 510, and 512, and lower repeating surface 514, 516, 518 and 519. The lower surfaces 514, 516, 518 and 519 are positioned over the top surface of the UV-cured polymer layer. An air or water sample medium 520 is placed in contact with the upper surfaces 506, 508, 510, 512 of the $TiO_2$ or $SiO_2$ layer 522.

As will be appreciated from inspection of FIGS. 28A-C, the "two-layer 2-D" grating structure includes a relatively deep BIND grating 504 in the Y dimension, characterized by upper and lower grating surfaces 506/508 and 510/512, respectively. The BIND aspect of the unit cell thus permits adding or more sample material and allows more material to adhere to the grating, permitting a greater resonance shift. The deeper grating in the BIND (Y direction) offers more surface area for binding biological material.

The ER grating 502 extending in the X direction, conversely, consists of a relatively shallow grating pattern with high regions 506 and low regions 508 (and also high region 510 and low region 512). In addition to providing good BIND detection capability, the grating is expected to simultaneously provide a wider TE ER resonance with optimal width.

An apparent advantage of the design of FIGS. 28A-C is that the ER and BIND structures should operate independently. Hence, structural dimensions optimized for either ER detection or BIND detection alone should work for the combination of the ER and BIND sensor of FIGS. 28A-C. While the specific dimensions for a structure having the unit cell of FIGS. 28A-C is of course variable, in one representative embodiment the BIND grating 504 has a period of between about 260 and about 1500 nm, and the depth of the grating (distance between surfaces 506 and 510) is between 100 nm and about 3000 nm. For the ER grating 502, the period is between about 200 nm and about 1000 nm, and the depth (Z distance between surfaces 506 and 508, and 510 and 512) is between 10 nm and about 300 nm.

Figure 30:
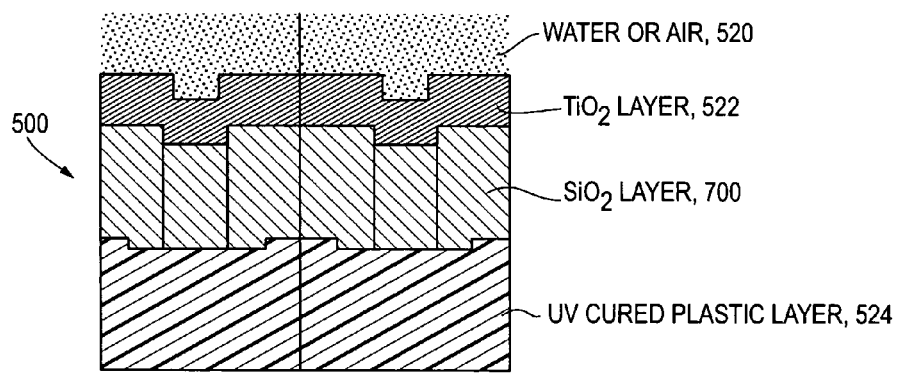
FIG. 30 is a cross-sectional view of a combined ER and BIND grating-based sensor in which an intermediate SiO2 layer is added between the UV-cured plastic grating layer and the high index of refraction layer forming the upper surface of the sensor.

The structure of FIGS. 28A-C was simulated on a computer using RCWA and its simulated reflection spectrum obtained, both with and without the addition of an ER grating structure in the X direction. FIG. 30 shows the BIND grating spectrum without the ER grating 502 in the X direction (curve 592), and the combined ER and BIND grating spectrum (curve 590). Both spectra simulations include water on the surface of the biosensor. The addition of the ER grating over the BIND grating (curve 590) creates additional resonance peaks (600 and 602) of width and location appropriate for ER excitation of a CY5 fluorophore. Note that the ER grating 502 (FIGS. 28A-C) and curve 590 also enhances total surface area thus offering the potential for BIND shift improvement. BIND peak wavelength values are indicated at peaks 606 and 604 in FIG. 30.

Further Applications for ER+BIND Biosensor Using Inhibitors

Consider further the following inhibition binding scenario, in which some fraction of the substance to be detected, e.g., protein, binds directly to the grating substrate (label-free) and some other fraction of the protein binds to an inhibitor having a fluorescent label. $K_s$ and $K_i$ are equilibrium binding constants for the substrate ($K_s$) and the inhibitor ($K_i$).

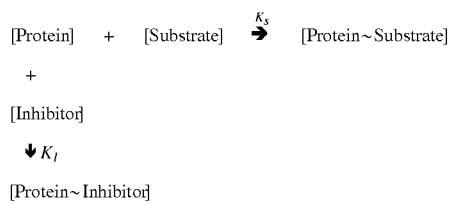

Mathematical equations can be written defining values and relationships for the concentrations and equilibrium binding constants (K) for the typical inhibition binding scenario above:

$$Ks=[\text{protein}\sim\text{substrate}]/[\text{protein}]\times[\text{substrate}] \quad (1)$$

and $$K_1=[\text{protein}\sim\text{inhibitor}]/[\text{protein}]\times[\text{inhibitor}] \quad (2)$$

Combining the two equations and rearranging terms, one can easily arrive at an equation for the fraction of protein bound by the substrate.

$$\text{Fraction of protein bound by the substrate} = \frac{1}{2PX - \sqrt{(X^2 - 4PS)}}$$

Where $X=(K_s+(K_s/K_i)*I+S+P)$ $K_i$ is the inhibition binding constant $K_s$ is the substrate binding constant and P, S, and I are the concentrations of the protein, substrate, and inhibitor, respectively.

In the setup of test reactions for new inhibitors, the operator generally only measures the amount of substrate bound, using for example some fluorescent label, but is unable to directly quantify the inhibitor ligand binding or the $K_1$ at the same time (i.e., the ligand binding is inferred). With two independent quantification methods provided by the combined ER and label-free biosensor of this disclosure, and a simple test, all of the variables for the binding scenario described above can be known. In other words, a more complete understanding and characterization of the binding properties are obtained using a single test using the inventive ER and label-free sensor.

The fluorescent label could be on the grating substrate surface or on the inhibitor. This means that either the substrate or the inhibitor could be label-less (label-free). A preferred embodiment uses a first binding molecule (that could the substrate of the biosensor) and a second potential binding molecule, e.g., inhibitor molecule, that may influence or compete with the binding of the biological substance (e.g., protein) with the first binding molecule.

This technique of using inhibitors to influence binding reactions in a label and label-free biosensor could be extended to encompass very tight binding interactions whereby a known competitive inhibitor with a weaker binding affinity could be employed to perturb/observe the much tighter binding entity.

In general, examples of specific binding substances (samples) which may be detected with the biosensor of this invention include nucleic acids, polypeptides, antigens, polyclonal antibodies, monoclonal antibodies, single chain antibodies (scFv), F(ab) fragments, F(ab')2 fragments, Fv fragments, small organic molecules, cells, viruses, bacteria, polymers, peptide solutions, protein solutions, chemical compound library solutions, single-stranded DNA solutions, double stranded DNA solutions, combinations of single and double stranded DNA solutions, RNA solutions and biological samples. Such biological samples could consists of, for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears and prostatic fluid.

The biosensor described herein may be used to detect (a) binding of components any of these types of samples to the biosensor surface, (b) binding of the sample to another component of the sample, e.g., a fluorophore in the sample, and (c) binding of the sample or sample component to a second sample which is added to the sample. As an example of binding (b), the sensor surface may bind to some component of the sample, such as for example streptavidin-biotin or 6His, and the biosensor may be used to detect the interaction of the bound component of the sample with an additional grouping of components in the sample, such as a polymerase complex. In the latter example of binding (c), a sample may have a component that is attached to the surface of the biosensor and another component which specifically binds/attracts another component(s) from a second sample that is placed on the biosensor.

Embodiments Using Natural Fluorescence

As a further embodiment, the combined ER and label-free biosensor is particularly useful for assays which utilize the natural fluorescence of biological molecules (i.e., without requiring the use of a bound fluorescence label), to make biophysical characterization measurements of folding, stacking, and changes and rates of changes to these upon interactions with other biological molecules and small test molecules. Such characterization measurements could be made with a bound fluorescence label, but such bound label is not necessarily required, especially for biological materials having an inherent fluorescence property.

The following table sets forth fluorescence characteristics of protein and nucleic acid constituents and coenzymes.

TABLE 1

Fluorescence Characteristics of Protein and Nucleic Acid Constituents and Coenzymes

| Substance | Conditions | Absorption $\lambda_{max}$ (nm) | Absorption $\epsilon_{max} \times 10^{-3}$ | Fluorescence $\lambda_{max}$ (nm) | Fluorescence $\Phi_F$ | Fluorescence $\tau_F$ (nsec) | Sensitivity $\epsilon_{max} \Phi_F \times 10^{-2}$ |
|---|---|---|---|---|---|---|---|
| Tryptophan | $H_2O$, pH7 | 280 | 5.6 | 348 | 0.20 | 2.6 | 11. |
| Tyrosine | $H_2O$, pH7 | 274 | 1.4 | 303 | 0.14 | 3.6 | 2.0 |
| Phenylalanine | $H_2O$, pH7 | 257 | 0.2 | 282 | 0.04 | 6.4 | 0.08 |
| Y base | Yeast tRNA$^{phe}$ | 320 | 1.3 | 460 | 0.07 | 6.3 | 0.91 |
| Adenine | $H_2O$, pH7 | 260 | 13.4 | 321 | $2.6 \times 10^{-4}$ | <0.02 | 0.032 |
| Guanine | $H_2O$, pH7 | 275 | 8.1 | 329 | $3.0 \times 10^{-4}$ | <0.02 | 0.024 |
| Cytosine | $H_2O$, pH7 | 267 | 6.1 | 313 | $0.8 \times 10^{-4}$ | <0.02 | 0.005 |
| Uracil | $H_2O$, pH7 | 260 | 9.5 | 308 | $0.4 \times 10^{-4}$ | <0.02 | 0.004 |
| NADH | $H_2O$, pH7 | 340 | 6.2 | 470 | 0.019 | 0.40 | 1.2 |

*Values shown for $\Phi_F$ are the largest usually observed. In a given case actual values can be considerably lower.
Source: Charles R. Cantor and Paul R. Schimmel, parts 1-3 Biophysical Chemistry - The behavior and study of biological molecules, W. H. Freeman and Company, New York, (1980), page 443.

This technique is especially important with nucleic acid polymers (DNA, RNA) (fluorescent nucleoside bases) stacking and hybridization, proteins (fluorescent amino acids phenylalanine, tryptophan, and tyrosine) and lipid membranes (enhancement and quenching effects upon incorporation of fluorophores into their different compartmentalizations). In one embodiment, the label-free BIND feature allows the quantification of the amount of sample material or ligand bound thereto and the ER feature allows the sensitive tracking of the biophysical change.

ER and BIND Biosensor with Additional Low Fluorescence SiO2 Layer to Reduce Background Fluorescence When the combined ER and BIND sensor of this disclosure is used for detecting fluorescence from a bound fluorophore or natural fluorescence, it can be useful to reduce background fluorescence emitting from within the biosensor construction materials so as to be able to generate fluorescence measurements with a higher signal to noise ratio. One way of accomplishing this is to deposit an additional layer of low fluorescence $SiO_2$ material onto the UV-cured polymer layer and then deposit the uppermost high index (e.g., $TiO_2$) layer onto the $SiO_2$ layer. Such a biosensor is shown in FIG. 30, and includes UV-cured polymer layer 524 (which is bound to a substrate sheet, not shown), intermediate $SiO_2$ layer 700, and upper $TiO_2$ layer 522. A sample in either an air or water-based medium is placed on the $TiO_2$ layer. The thickness of the additional $SiO_2$ layer 700 will depend on such factors as the grating duty cycle and required background fluorescence level, but generally will be in the range of 500 to 5000 Angstroms.

The $SiO_2$ 700 layer preferably has low native fluorescence in response to incident radiation from light sources used to interrogate the biosensor. The fluorescence level in $SiO_2$ depends on the process by which it is made, and its structure (amorphous vs. nanocrystalline), may also play a role. Full oxidation of the $SiO_2$ molecules in the layer ($SiO_2$), as compared to say $SiO_{1.95}$, also appears to be important in providing a layer with low fluorescence. Preferably, the $SiO_2$ layer is made by a process, and has a structure, which results in relatively low native fluorescence.

One example of the use of $SiO_2$ intermediate layers would be in the structure of FIGS. 28A-C, wherein below the top $TiO_2$ layer 522, a layer of low fluorescence $SiO_2$ is applied over a UV-cured polymer layer. The $SiO_2$ intermediate layer is of uniform thickness in both the X and Y directions.

The additional layer of low fluorescence $SiO_2$ material may also be present in the other biosensors described previously in this document.

It will be appreciated that in FIGS. 28 and 30 and in other figures showing the upper high refractive index layer, $TiO_2$ is not a required material for the upper layer 522. $Ta_2O_5$ (tantalum pentoxide) could work also. $TiO_2$ has a higher refractive index than $Ta_2O_5$, which is why it is generally used for a high refractive index layer. When using $Ta_2O_5$, it takes more physical thickness to achieve the same optical thickness. In the examples presented herein, the range of thickness for the upper layer 522, whether using $TiO_2$ or $Ta_2O_5$, is between about 70 nm to 250 nm.

In one further possible embodiment a hafnium oxide coating is applied to a biosensor as a high index of refraction layer, replacing $TiO_2$ or $Ta_2O_5$. At infrared and visible wavelengths, $TiO_2$ or $Ta_2O_5$ have no absorption. However, at low wavelengths, these materials all start to absorb, and the absorption increases as one goes to lower and lower wavelengths. This is a problem for resonant devices, because the absorption has the effect of diminishing the resonance (i.e. no peak will be measured, or the peak will be small). Hafnium oxide does not happen to have absorption, even for wavelengths as low as 400 nm. The thickness of the hafnium oxide coating and grating dimensions would be selected to yield resonance at the UV wavelengths of interest.

Use of ER Sensor with Time Resolved Fluorescence (TRF) and Fluorescence Polarization (FP) Measurements One further example of the novel uses of the present ER and BIND sensor is the use of the sensor for time resolved fluorescence (TRF) and fluorescence polarization measurements. TRF and FP polarization are two methods that would benefit greatly from enhanced signal derived from the combined label-free and ER device of this disclosure. These two methods are especially useful for separating specific ER signals for binding events from background signals and from molecules not participating in the binding event. The fluorophore would need to be matched to the wavelength enhancement capability of the sensor.

The invention of a method for using ER with FP and/or TRF offers a user the opportunity to cleanly detect the presence of a fluorophore involved in a binding event and discriminate such detection from background or non-participating molecules, and with much higher sensitivity.

FP and TRF are widely used techniques in the diagnostic and pharmaceutical test protein/compound screening industries. See for example U.S. Pat. Nos. 6,432,632, 6,207,397, 6,159,750, 6,448,018, 6,455,861, 6,566,143, and 5,504,337, the contents of each of which are incorporated by reference herein. See also the patents of Budach et al., U.S. Pat. Nos. 6,870,630 and 6,707,561, and the patents of Neuschäfer et al., U.S. Pat. Nos. 6,078,705 and 6,289,144. The methods are popular because they allow for discrimination of binding signals from unwanted signals such as background and non-binding molecules. The current methods would have improved signal to noise ratios (sensitivity) and allow for reduced reagent consumption. These improvements will be especially useful in the area of study known as proteomics where sensitivity and reagent are limiting. In addition the typical sorts of biophysical determinations (folding, proximity to other molecules, size, etc.) would be enhanced as well.

By offering the potential of 50-100× improved sensitivity in determining binding interactions, these techniques also have several commercial advantages, including reduced reagent consumption, and greater confidence limits in low signals It is believed that any instrument that can measure FP from the underside of a clear bottom plate would work for the ER/BIND biosensors described herein. There are instruments commercially available that can measure both FP and TRF, such as for example the Molecular Devices SpectraMax M5 instrument. However, the instrument for detection of FP measurements does not have to be the same instrument that makes TRF measurements.

The physical characteristics of the ER biosensor that make it more advantageous for FP or TRF measurements, by providing a greatly improved signal and signal to noise ratio, is the grating structure of the biosensor (as described at length in this document) that creates the resonance effect for enhanced signal. FP and TRF are recommended methods for pharmaceutical screening activities because they allow users to avoid unwanted signals coming from the natural fluorescence of the compounds they are screening (i.e. noise/background much higher with these compounds).

Spotting Process and Quality Control with ER and BIND Sensor

In one possible use of the biosensor of this invention, the ER and BIND sensor is used to analyze a sample in a multitude of locations, each of such locations defining a microarray spot of about 10-500 microns in diameter.

The term "spot" refers to a small quantity of sample material which is placed on the surface of the biosensor. One produces such spots by depositing tiny droplets of target solution containing the sample on the surface of the biosensor and letting them dry. The droplet size determines spot size. Different processes exist for depositing the droplet and such techniques are generally known in the art. In one possible implementation, the sensor surface comprises many spots in an array (i.e., a microarray of spots), most of which have differing compositions.

One then applies a common test material of varying complexity to the entire array. In one example, this test material comprises a fluorescently labeled test material. The sensor is then interrogated with light to look for binding between the test material and the spot. To analyze a biosensor in the form of a microarray with a multitude of spots, one obtains an image of the biosensor showing all the spots (see the imaging readout instrument in the embodiment of FIG. 25 discussed below) and uses image analysis techniques or separate capture of spectrographic data from each spot to determine the signal (intensity and shift in peak wavelength value) from each spot. Each spot provides one data point. The image must have a resolution dimension (pixel size) below the spot size.

Process variability during spotting (e.g. DNA spotting) of sample materials onto an assay surface leads to indeterminate results for subsequent binding of test samples. Uncontrolled variation in the density of sample material, and among spots, significantly hinders quantitation of test material binding frequency by fluorescence signal. Quantifying the sample material by applying a second label is generally not practical.

The combined ER and label-free biosensor of this disclosure overcomes these problems. In particular, the BIND signal is used to quantify the amount of material in the spot rapidly in a non-destructive way, without the use of fluorophores or other added labels. The BIND measurements are made prior to exposure of the sample (spots) to the fluorophore-labeled test material. The ER measurements are made after exposure of the sample to the fluorophore-labeled test material. The BIND measurements thus provide a normalizing quantity for the fluorescence signal from each spot. A BIND image of the spotted array also provides information regarding spot morphology and can thus serve a quality control function for the spotting process.

Figure 31:
FIG. 31 is an image of a microarray of spots deposited on a grating-based sensor (which may or may not be optimized for both ER and BIND measurements).
Figure 32:
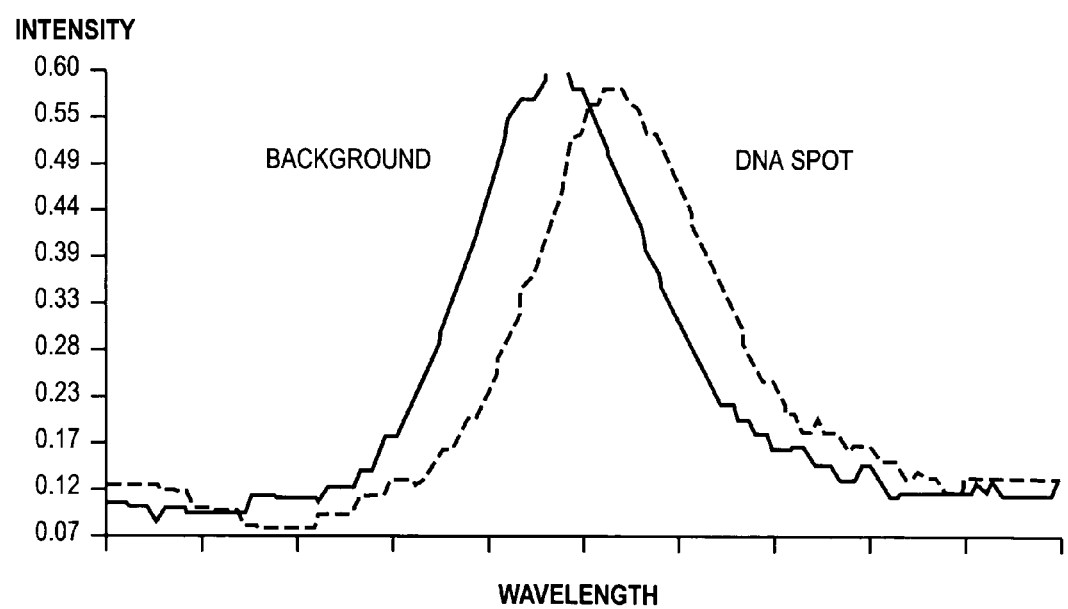
FIG. 32 is a graph of a peak shift for one of the spots of FIG. 31 due to presence of a DNA sample being placed on the sensor.
Figure 33:
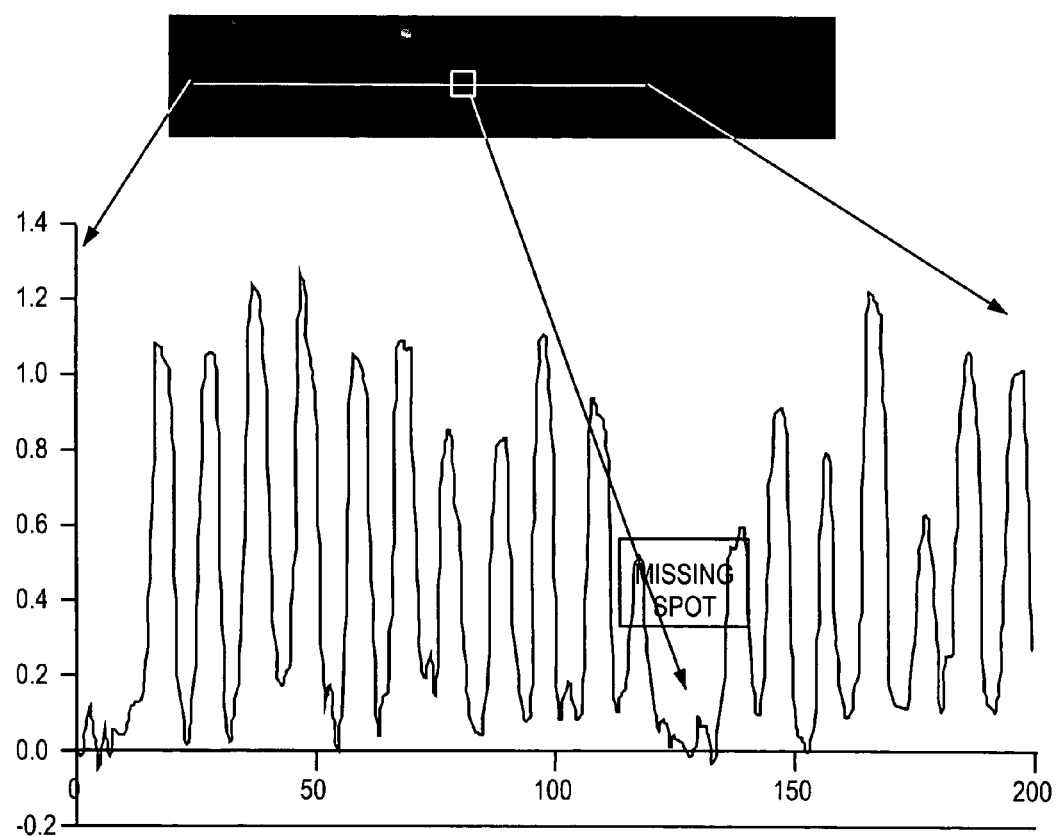
FIG. 33 is an illustration of a row of spots showing the shift in peak wavelength value in nanometers (which is quantitatively related to the amount of DNA in the spot) as a function of position and showing a missing spot (dark location in the row of spots), the missing spot indicated by the low region in the graph.

One representative embodiment will now be described in conjunction with FIGS. 31-33. FIG. 31 is an image of a microarray of spots deposited on a grating-based sensor (which may or may not be optimized for both ER and BIND measurements) at 7 micron resolution. The image is captured by a CCD camera (see the embodiment of FIG. 25 discussed below). The DNA spots may be imaged at various micron resolution (pixel size), such as 7 micron, 15 micron and 30 micron. FIG. 32 is a graph of a peak shift for one of the spots of FIG. 31 due to presence of a DNA sample being placed on the sensor. The shift is indicated by movement of the peak wavelength value to the right for the DNA spot. The amount of this shift is a quantitative measure of the quantity of DNA present on the spot. FIG. 33 is an illustration of a row of spots and a corresponding graph of PWV shift (in nanometers) as a function of position along the row. The variation in PWV shift is a quantitative measure of the amount of DNA located on the spots in the row. The area on the sensor surface that is missing the spot of DNA sample material is shown as the dark location in the image of the row of spots), the missing spot also indicated by the low region in the graph. The graph of FIG. 33 thus provides further a further qualitative and quantitative measure of the amount of DNA on the spots in the array.

The spotting aspects of this disclosure thus provides a method for analysis of thickness, uniformity and morphology of DNA spots (or in general spots of any biological material such as RNA, protein, carbohydrates, peptides etc.) on nanostructured optical surfaces such as those used in the BIND label-free technique. The method is suitable for use both in nanostructured optical surfaces such as the combined ER and label free sensor described herein. It can also be used for analysis of spots on a grating structure which is just designed for one technique or the other.

Quality control of printed microarrays is important for both manufacturers and users of microarrays. The printed DNA spots often do not have a recognizable label or tag attached to them (such as fluorescent, quantum dot, radioactivity). This makes it difficult to image printed spots for quality assurance quickly and reliably and quantitatively before an assay is performed. The variation in the amount of DNA printed on the spots has a profound effect on the outcome of hybridization assays and is particularly critical in diagnostics related applications. In view of these issues, the inventive spotting process aspect of this disclosure provides a non-destructive, non-contact method to image as-printed DNA spots on nanostructured optical surfaces (sensor surfaces). This invention can be used to ascertain the quality and reliability of DNA spot printing process and weed out defective microarrays thereby reducing the cost of manufacturing such microarrays. This invention can also be used to normalize final results from labeled assays performed using these chips (via fluorescence etc) to amount of material originally spotted, providing information on binding affinity/efficiency not previously available by other means.

The methods of this disclosure are preferably performed in a non-contact, non destructive manner. That is, the spots are imaged via optical means and both quantitative and qualitative information is obtained as to the spots as explained in FIGS. 31-33. This method is believed superior over prior art methods which use random-sequence-short-oligonucleotides that contain a labeled end (such as a fluorescent tag) which weakly binds to the single stranded DNA on the surface of the chip. The fluorescence signal from the bound spots is indicative of the amount of DNA present in the spots. These methods are often plagued by problems such as dissociation at room temperature (due to low melting point of random-labelled-oligo and DNA complex), streaking, spotting, non-specific binding to the substrate and thereby increasing background and in some cases complete removal of the bound DNA from the spots owing to the use of detergents in these QC tests. Perkin Elmer has used reflective imaging to non-destructively determine the presence and absence of spots using reflected laser light from salt crystals present in the DNA spots. This is a purely qualitative (yes or no) method and does not work when the printing solution does not use salt or if the salt crystals are washed off from the spotted array.

The functional advantages of the imaging technique of this aspect of this disclosure is that it provides a quantitative analysis of amount of material bound to structured optical surface. It is non-destructive and non-contact based measurement method. Furthermore, the invention could be used by manufacturers and users of microarrays to ascertain the quality (uniformity, spot morphology and quantity of material bound) of the spots on the microarray surface. Further, the analysis takes approximately one minute, instead of the considerably longer period required in prior art. This allows analysis to be performed on every microarray, rather than smaller samples.

Readout Systems for Biosensors Combining Label-Free Detection and Fluorescence Amplification (ER)

With the above description of combined ER and label-free biosensors in mind, this document will now describe several embodiments of a readout and detection system useful for interrogating the sensor and acquiring both label-free and ER data from a single binding site on the detector.

Figure 25:
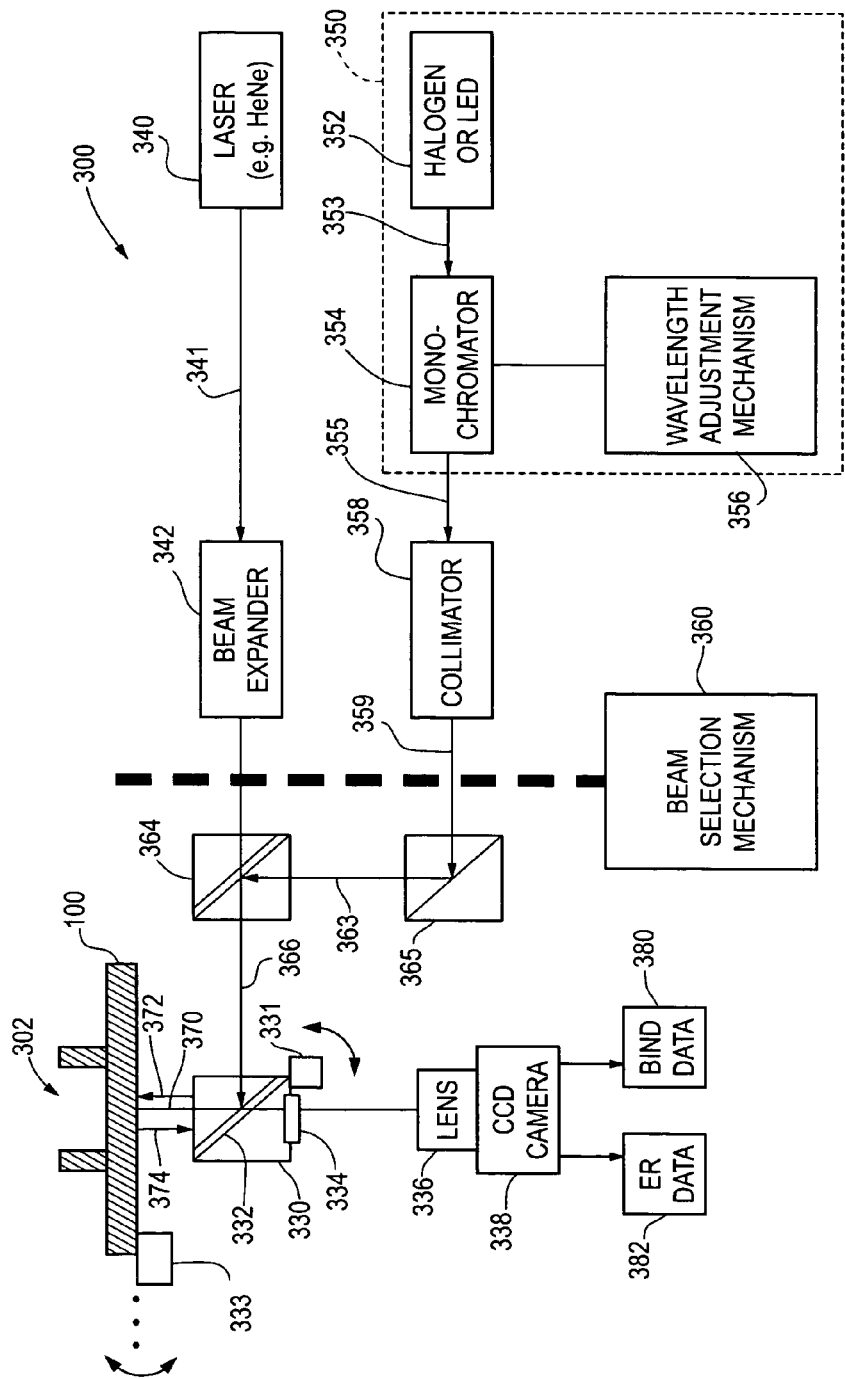
FIG. 25 is a schematic drawing of an imaging readout system for a combined ER and label-free grating-based sensor.

A first embodiment of a readout and detection system 300 is shown schematically in FIG. 25. The system 300 of FIG. 25 is an imaging readout system. The biosensor 100 is designed to exhibit both a sharp resonant peak, in the optical spectrum, for label-free detection and a high electromagnetic field in the evanescent region of the biosensor for significant enhancement of fluorescence signal. The readout system reads out both of these effects, taking advantage of these biosensor properties. This disclosure provides a novel imaging readout system with the capability to measure either or both signals from the biosensor.

The biosensor 100, referred to herein as a "comBIND sensor" herein, is interrogated optically from the bottom side of the sensor. On the topside of the biosensor 100, the biosensor may be immersed in water or another liquid, or it may be exposed to air. Any molecular or cellular binding interaction, which the biosensor is designed to detect, takes place on the topside of the biosensor 100. The biosensor 100 may be part of a larger assay device that includes liquid containing vessels, such as for example a microwell plate having e.g., 8 columns of wells, each row containing 12 wells. The biosensor may also be a component of a microarray slide. In the illustration of FIG. 25, a single well (detection site) 302 is shown in cross-section, it being understood that dozens, hundreds or even thousands of such detection sites may be present.

The imaging readout and detection system 300 includes an ER light source 340 in the form of a laser (e.g., HeNe laser), a broader spectrum BIND light source 350 including as a halogen white light source or a LED 352, and a CCD camera system 338 serving as a common detector to capture both ER and label-free data in successive images. The system 300 includes an optical beam combining subsystem that includes dichroic mirrors 364 and 330 which serves to combine and direct incident light 372 from the light sources 340 and 352 onto the biosensor. The dichroic mirror 330 collects signal light for detection and directs it to a lens 336 where it is imaged by the CCD camera 338.

The light beam 370 present below the biosensor 100 consists of illumination light 372 and reflected light 374. The reflected light 374 includes direct reflection and fluorescent emission if there is fluorescent material present on the biosensor.

Signal detected by the CCD camera 338 through a lens system 336 is processed electronically or by computer algorithm to become BIND (label-free) data 380 or ER data 382. Such data may be stored, displayed, and analyzed on an analytical instrument such as a computer or workstation for the instrumentation shown in FIG. 25 (not shown, but having access to data 382 and 380) by the user of the readout system 300. Furthermore, the combination of the BIND data 380 and the ER data 382 allows the user to gain information on binding interactions or cell interactions that is unique to the novel biosensor 100.

In the illustrated design, the optical components 340, 350 and 330 are designed to produce a single beam 372 of incident radiation and the biosensor is moved in X and Y directions to thereby sequentially obtain data from all the wells 302 or binding sites on the biosensor 100 surface. Such motion may be produced by placing the biosensor 100 on an X-Y motion stage (not shown), of which persons skilled in the art are familiar. When a given well or binding site 302 is in position such that the well 302 is in registry with the beam 372, in one embodiment the light sources 340 and 350 are operated in succession (or selectively allowed to direct radiation onto the biosensor) and first and second images are captured by the CCD camera 338, one an ER image and the other a BIND image. The successive collection of CCD images could be facilitated by use of the beam selection mechanism 360 (such as a shutter), which selectively allows light from either the source 340 or the source 350 to pass to the dichroic mirror 330 and be reflected onto the biosensor. Beam selection can also be done electronically, such as by electronically controlling the on and off times of the light sources 340 and 350. Alternatively, both light sources could be activated at the same time and the selection mechanism 360 operated to pass both beams so that the incident beam 372 contains light from both sources. In this situation, the CCD camera 338 would capture a single image containing both ER and BIND information. Image processing techniques would then be applied to the resultant image from the CCD camera 338 to extract the BIND and ER components of the composite image.

The ER light source 340 may be a laser, such as a helium-neon (HeNe) laser. The laser beam 341 further goes through a beam-conditioning device 342 such as a beam expander.

The beam expander 342 expands a small diameter laser beam into a large diameter laser beam. The output beam 343 is collimated and linearly polarized. The biosensor produces the ER effect in response to incident light at a specific polarization. Polarization may be achieved by using a laser designed for producing a linearly polarized output laser beam.

The BIND (label-free) light source 350 may consist of a halogen or LED light source 352, and a monochromator 354 with a wavelength adjustment mechanism 356. The light beam 353 emitted by the light source 352 is broadband in nature, while the light beam 355 at the exit port of the monochromator 354 is monochromatic.

The output light beam 355 from the monochromator 354 is conditioned by a beam conditioning device 358, which may be a collimator. A mirror 365 directs the light beam 349 from the output of the conditioning device 358 to the dichroic mirror 364. The combined light from the light sources 340 and 350 is shown at 366 where it is directed to the beam splitting and combining assembly 330 which then directs it to the bottom surface of the biosensor 100.

The BIND light source 350 may also consist of a tunable laser. In that case, the beam-conditioning device 358 is a beam expander. Note also that a tunable laser or flash lamp could serve as a single illumination source for both BIND and ER measurements.

In addition, since polarized light facilitates detection of a BIND signal, there may be a polarizer within the light source 352 so that the light 363 is linearly polarized. Alternatively, the light-directing element 365 may be a polarizing beam splitter to transform a randomly polarized light 359 into a linearly polarized light 363.

For detection of the laser excited fluorescence signal, the beam splitting and combining assembly 330 incorporates a set of optical filters 332 and 334. Filter 332 is a dichroic filter that reflects the laser light while transmitting fluoresced light from the sample. Filter 332 also functions as a beamsplitter in the BIND wavelength range, which is 830 nm to 900 nm in one preferred design. Filter 334 only allows transmission of light within two wavelength ranges: laser excited fluorescence and the BIND wavelength range. An imaging lens 336 may be used to collect the fluorescence light at the biosensor surface and focus it on the focal plane of the CCD camera 338.

The design of FIG. 25 also includes rotation apparatus to rotate the biosensor relative to the incident beam 372 for purposes of ER detection. In one possible embodiment, a rotation device 331 is attached to the beam splitting and combining assembly 330 and rotates the assembly 330 as indicated by the arrows (thereby providing for rotation of the incident beam about angle θ). In an alternative embodiment, rotation device 331 is omitted and instead a rotational device 333 is attached to the XY motion stage which operates to rotate the XY motion stage (and biosensor 100 mounted thereon) relative to the (fixed) incident beam 372, as indicated by the arrows to the left of device 333 in FIG. 26.

Additional lenses, mirrors and optical filters may be incorporated into the readout system to achieve desired performance. Properly designed optical filters may be used to eliminate undesired cross-talk between BIND detection and ER detection. In addition, a beam selection mechanism in the form of electronic or mechanical shutters 360 may be used to properly synchronize light illumination and detection of the two channels, so that only one light source illuminates the biosensor at a given time, to eliminate any cross-talk.

A significant advantage of the biosensor readout system described in FIG. 25 is that both BIND and ER data may be collectedly simultaneously (or in rapid succession) at the same biosensor location. High-resolution imaging methods are useful for high content bioassays such as cell-based assays or microarrays.

An integrating single point detector may replace the CCD camera 338. In that case, the system produces an image by synchronizing sensor motion, over the location of the incident radiation 372, with the detector output.

Further details on use of a CCD camera to obtain ER data from a biosensor can be found in the technical literature, e.g., an article of Dieter Neuschäafer, Wolfgang Budach, et al., Biosensors & Bioelectronics, Vol. 18 (2003) p. 489-497, the contents of which are incorporated by reference herein.

Figure 26:
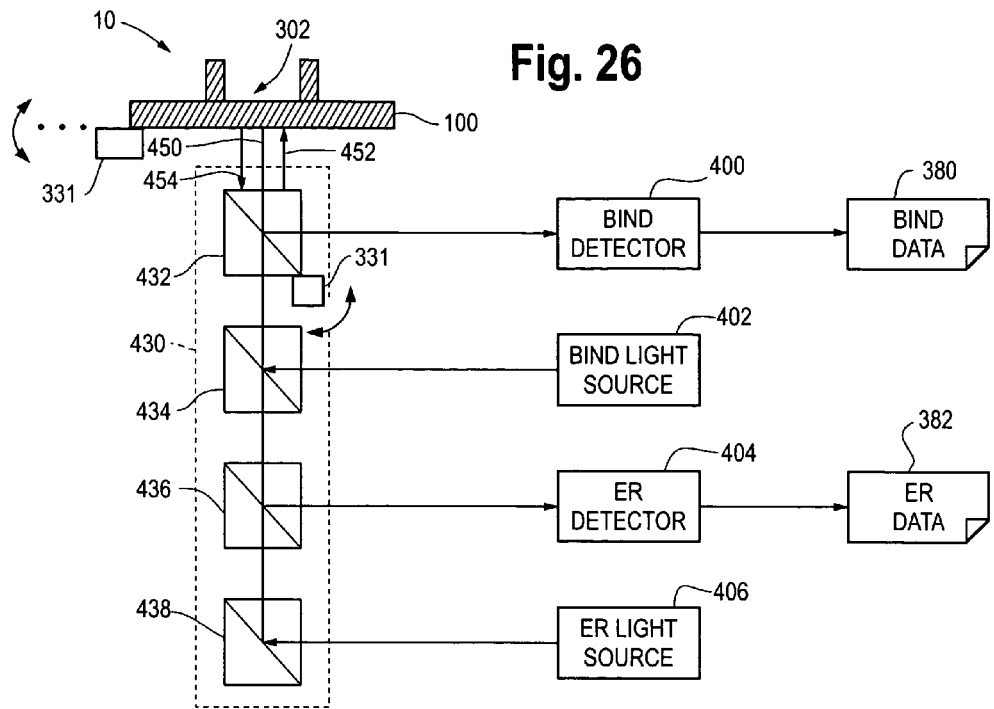
FIG. 26 is a schematic illustration of a second readout system for a combined ER and label-free grating-based sensor.

A second embodiment of a readout and detection instrument 300 is shown in FIG. 26. Whereas the design of FIG. 25 is an imaging readout system, the design of FIG. 26 is not an imaging system. As before, the biosensor 100 is designed to exhibit both a sharp resonant peak in optical spectrum for label-free detection and a high electromagnetic field in the evanescent region of the biosensor for significant enhancement of fluorescence signal. Because of these properties of the biosensor, a system that reads out both of these effects is required. FIG. 26 describes an additional novel readout system that measures either or both signals from the biosensor.

The biosensor 100 is interrogated optically from the bottom side at the location of a binding site (e.g., well 302). The topside of the biosensor 100 may be immersed in water or another liquid, or may be exposed to air. Any biomolecular or cellular binding interaction, which the biosensor is designed to detect, takes place on the topside of the biosensor. Any of the measurement systems described herein could also read the biosensor 100 from the top (binding side), if desired, using appropriate focusing apparatus.

As noted above, the sensor 100 may be part of a larger assay device that includes liquid containing vessels, such as a microwell plate. The biosensor may also be a component of a microarray slide.

The readout system 300 includes a BIND light source 402, a BIND detector 400, an ER light source 406, and an ER detector 404. An optical system 430 serves to combine light from the sources 406 and 402 and direct such light as an incident beam 450 onto the bottom surface of the biosensor 100. The optical system 430 further collects reflected light 452 from the biosensor and directs such reflected light to the detectors 400 and 404. The optical system 430 consists of four light beam splitting and combining components, one (432) for the BIND detector, one (434) for the BIND light source, one (436) for the ER detector, and one (438) for the ER light source. The light beam 450 present below the biosensor consists of incident light 452 and returned light 454. The returned light 454 includes reflected light and fluorescent emission if there is fluorescent material present on the biosensor.

Signal detected by the BIND (label-free) detector 400 is processed electronically or by computer algorithm to become BIND data 380, which is stored, displayed, and analyzed on a computer (not shown) by the user of the readout system. Similarly, signal detected by the ER detector 404 is processed and transformed into ER data 382 for the user. Furthermore, the combination of BIND data 380 and ER data 382 allows the user to gain information on binding interactions or cell interactions unique to the novel biosensor.

The embodiment of FIG. 26 also includes either a rotation device 331 for rotating the incident light beam 452 relative to the biosensor 100, or a rotation device 333 for rotating the XY stage and biosensor 100 relative to the incident light 452. The placement of the rotation device 331 may be such that the entire assembly 430 is rotated.

Figure 27:
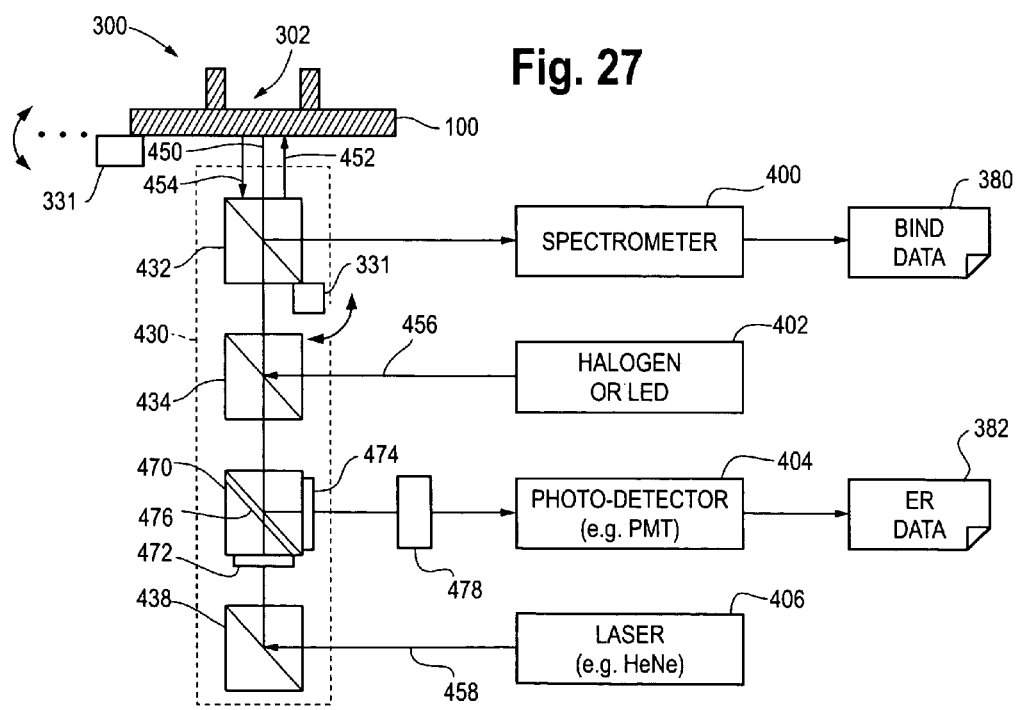
FIG. 27 is a more detailed illustration of the embodiment of FIG. 26.

FIG. 27 depicts a readout system like that shown in FIG. 26, but with more detail. The BIND detector 400 in this embodiment is a spectrometer. The BIND light source 402 may take the form of a tungsten halogen light bulb or a light emitting diode (LED). The ER detector 404 comprises a photo-detector, such as a photomultiplier tube (PMT). The ER light source 406 is preferably a laser producing a beam with a wavelength within the excitation band of the fluorophore for use with the biosensor, such as a helium-neon (HeNe) laser for excitation of the CY5 fluorophore.

The light beam 456, emitted from the BIND light source 42, is nominally collimated light for detection of the BIND signal. Thus, the light source 402 may incorporate a collimation lens. In addition, since use of polarized light improves detection of the BIND signal, the light source 402 may also incorporate a polarizer so that the light 456 is polarized. Alternatively, the beamsplitter 434 may be a polarizing beamsplitter to transform a randomly polarized light 456 into a linearly polarized light incident on the bottom of the biosensor 100.

The light beam 458 from the laser 406 is a collimated beam. ER performance improves if the laser beam has linear polarization. Polarization may be achieved by using a laser designed to produce a linearly polarized beam.

For detection of the laser-excited fluorescence signal from the biosensor 100, the beam splitting and combining assembly 436 includes a set of optical filters 472, 474, and 476. Filter 472 allows the incident laser beam 458 from the laser source 406 to transmit through the beam splitting and combining element 436. Filter 476 is a dichroic filter that transmits the laser light from the source 406 while reflecting the fluoresced light from the biosensor 100 in the direction of the detector 404. Filter 474 only allows transmission of fluoresced light to be directed at the photo-detector 404. An imaging lens 478 may be used to collect the fluorescence from the biosensor surface more efficiently.

Additional lenses, mirrors and optical filters may be incorporated into the readout system to achieve desired performance. Properly designed optical filters may be used to eliminate undesired cross-talk between BIND detection and ER detection. In addition, electronic or mechanical shutters may be used to properly synchronize light illumination and detection of the two channels, so that only one light source illuminates the biosensor at a given time, to eliminate any cross-talk.

As with the case with the design of FIG. 25, the optical components of the design of FIGS. 26 and 27 can be constructed and arranged to produce a beam 452 of incident radiation at one location while an XY motion stage moves the biosensor in X and Y directions to thereby sequentially obtain data from all the wells 302 or binding sites on the biosensor 100 surface. In one embodiment the light sources 402 and 406 operate in succession generating data successively at the detectors 400 and 404 from the given well or binding site 302 currently illuminated by beam 452. The successive collection of ER and BIND data could be facilitated by use of beam selection mechanism (such as a shutter), not shown in FIG. 26, or by electronic control of the light sources 402 and 406. Alternatively, both light sources could be activated at the same time so that the incident beam 452 contains light from both sources. In this situation, the detectors 400 and 404 obtain data simultaneously.

A significant advantage of the biosensor readout system described here is that both BIND and ER data may be collectedly simultaneously (or in rapid succession) at the same biosensor location. The BIND detector 400 and the ER detector 404 may be integrating detectors that obtain data from a single point per binding site or well but over a relatively large area, or imaging detectors, such as CCD detectors, that collect data pixel by pixel at a user specified resolution. High-resolution imaging methods are useful for high content bioassays such as cell-based assays or microarrays.

Figure 1:
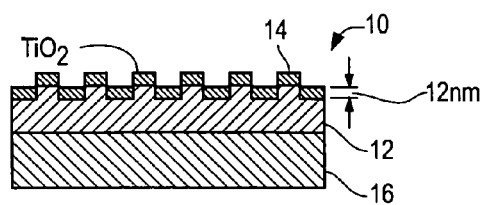
FIG. 1 is an illustration of a prior art biosensor arrangement.
Figure 2:
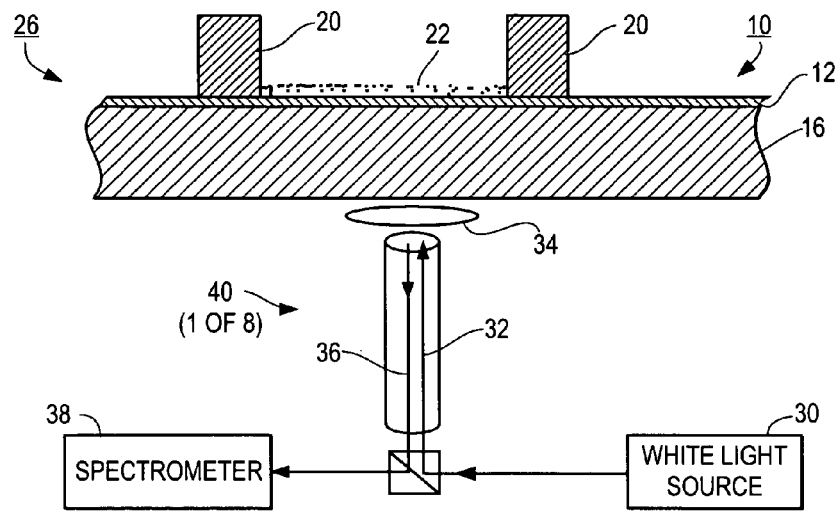
FIG. 2 is an illustration of a prior art biosensor and detection system for illuminating the biosensor and measuring shifts in the peak wavelength of reflected light from the biosensor.
Figure 3:
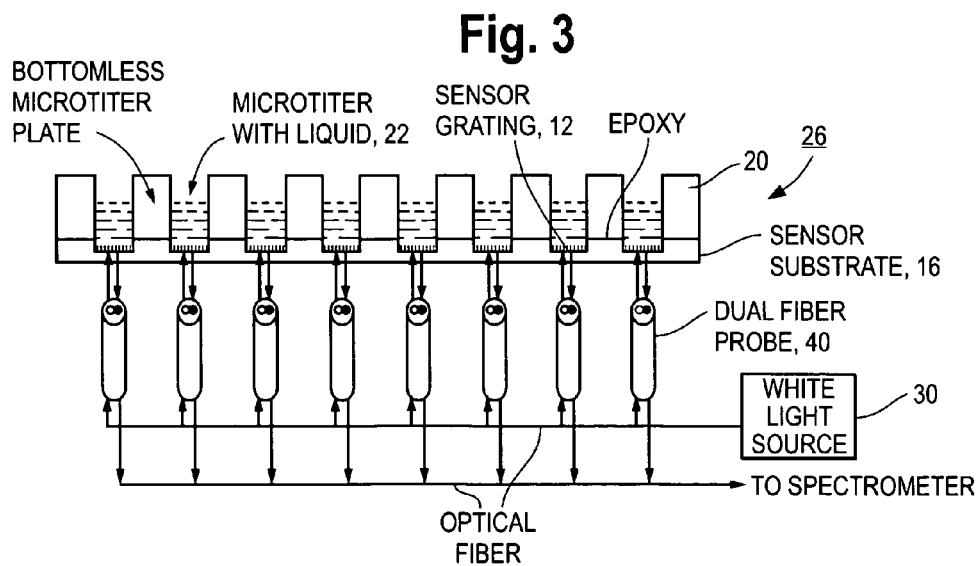
FIG. 3 is an illustration of an arrangement of 8 illumination heads that read an entire row of wells of a biosensor device comprising the structure of FIG. 1 affixed to the bottom of bottomless microtiter plate.

Furthermore, the optical structure of FIGS. 25, 26 and 27 can be replicated such that multiple wells or binding sites on the biosensor 100 can be interrogated and detected at the same time, e.g., taking advantage of the concepts shown in FIG. 3.

Readout System with Single Light Generating Source

It will be noted that the embodiments of FIG. 25 includes separate light sources 350 and 340 for BIND and ER measurements, respectively, and that the embodiment of FIG. 26 includes separate light sources 402 and 406 for BIND and ER measurements, respectively. In one possible variation, a single light source may be used for both BIND and ER measurements. This light source could take several possible forms, such as the form of a tunable laser, or a broad spectrum high intensity flash lamp. The output from the light source is optionally collimated, expanded with a beam expander (if a tunable laser is used as the source), passed through a monochromator or filter stage (if a flash lamp is used), and then directed to the surface of the biosensor. The optics used for detection of ER and BIND signals can take the form of the apparatus shown in FIGS. 25-27 and described above.

In one embodiment, to obtain both BIND and ER data from a given binding site in the biosensor, the light source can be activated twice in order to select different wavelength ranges for illumination (one for BIND and one for ER). For example, the BIND detector obtains BIND data in the first activation of the light source and the ER detector obtains ER data in the second activation.

In one possible variation, in the case of a broad band source (i.e. Xenon flash lamp), one can also illuminate the biosensor with a broad spectrum and simultaneously collect BIND and ER data by splitting the return signal and diverting it through two different filter stages. For simultaneous BIND/ER illumination/collection, one needs to illuminate the plate at some angle of incidence. The specular (direct) reflection component contains a BIND peak, and its spectral position is determined by a monochrometer. A lens system, or even an integrating sphere, collecting only light leaving the surface at angles other than the incidence angle, will provide a relatively clean ER signal after passing through a filter or monochrometer that selects the emission range for the fluorophore of interest.

While a number of exemplary aspects and embodiments have been discussed above, those of skill in the art will recognize certain modifications, permutations, additions and sub-combinations thereof as being present in the disclosure. It is therefore intended that the following claims and claims hereafter introduced are interpreted to include all such modifications, permutations, additions and sub-combinations as are within their true spirit and scope.

In the claims, the term "evanescent resonance (ER) detection" or "evanescent resonance (ER) detection mode" is intended to encompass the detection of fluorescence, phosphorescence, chemi-luminescence, electroluminescence, or other type of luminescence, for example as described in Budach et al., U.S. Pat. No. 6,707,561. Such luminescence could be attributable to native luminescence of the sample material or to a bound substance, e.g., fluorescence label, or quantum dots (luminescent metals). Such bound substance may be bound to the sample being tested, the surface of the biosensor, or both.

We claim:

1. A method of analyzing at least one sample, comprising the steps of:

placing the at least one sample on a sensor comprising a substrate having a periodic surface grating structure, wherein the periodic grating structure is constructed in a manner designed for both (1) optical interrogation of the biosensor in an evanescent resonance (ER) detection mode and (2) optical interrogation of the biosensor in a label-free detection mode;

illuminating the sensor in a readout detection instrument with light from at least one light source designed for the ER detection mode and illuminating the sensor with the at least one light source designed for the label-free detection mode; and analyzing light reflected from the sensor, the analyzing step providing information regarding the sample.

2. The method of claim 1, wherein the at least one sample is in an air medium, and wherein the light from the at least one light source has a polarization perpendicular to the grating structure.

3. The method of claim 1, wherein the at least one sample is in a liquid medium, and wherein the light from the at least one light source has a polarization parallel to the grating structure.

4. The method of claim 1, wherein the light from the at least one light source has a wavelength selected to activate a fluorophore bound to the sample.

5. The method of claim 1, wherein the light from the at least one light source has a wavelength selected to activate a native fluorescence of the sample.

6. The method of claim 1, wherein the at least one light source illuminates the sensor in the near infra-red portion of the spectrum.

7. The method of claim 1, further comprising the step of combining the light from the first and second light sources into an incident beam and illuminating the biosensor with the beam.

8. The method of claim 1, further comprising the step of collecting the reflected light and directing it to an imaging device.

9. The method of claim 1, further comprising the step of collecting the reflected light in an integrating detector.

10. The method of claim 9, further comprising the steps of moving the sensor in X and Y directions relative to the beam to thereby interrogate multiple detection areas of the biosensor, and generating ER detection mode and label-free detection mode data for each of said multiple detection areas.

11. The method of claim 1, wherein the at least one light source comprises a first label-free light source and a second ER light source, and wherein the method further comprising the step of selectively illuminating the sensor with light from the first and second light sources.

12. The method of claim 1, further comprising the steps of moving the sensor in X and Y directions relative to light from the at least one light source to thereby interrogate multiple detection areas of the sensor, and generating ER detection mode and label-free detection mode data for each of said multiple detection areas.

13. The method of claim 1, wherein the at least one sample is selected from the group of samples consisting of molecules having a molecular weight of less than 1000 daltons, molecules with a molecular weight of between 1000 and 10,000 daltons, amino acids, proteins, nucleic acids, lipids, carbohydrates, nucleic acid polymers, viral particles, viral components, cellular components, and extracts of viral or cellular components, polypeptides, antigens, polyclonal antibodies, monoclonal antibodies, single chain antibodies (scFv), F(ab) fragments, F(ab')2 fragments, Fv fragments, small organic molecules, cells, viruses, bacteria, polymers, peptide solutions, protein solutions, chemical compound library solutions, single-stranded DNA solutions, double stranded DNA solutions, combinations of single and double stranded DNA solutions, RNA solutions and biological samples.

14. The method of claim 13, wherein the biological samples comprise samples selected from the group of consisting of blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears and prostatic fluid.

15. The method of claim 1, wherein a fraction of the sample is bound to an inhibitor.

16. The method of claim 15, wherein the inhibitor is bound to a fluorescent label.

17. The method of claim 1, wherein the method further comprises the step of detecting the binding of a component of the sample to the periodic grating structure.

18. The method of claim 1, wherein the ER detection mode detects natural fluorescence of the sample.

19. The method of claim 1, further comprising the step of applying a fluorescent label to the sample and acquiring time resolved fluorescence measurements from the sensor.

20. The method of claim 1, further comprising the step of applying a fluorescent label to the sample and acquiring fluorescence polarization measurements from the sensor.

21. The method of claim 1, wherein the grating structure comprises a two-dimensional grating structure, and wherein:

the first dimension of the periodic grating structure comprises a grating structure designed for label-free detection, and the second dimension of the periodic grating structure comprises a grating structure designed for ER detection.

22. The method of claim 1, wherein the grating structure further comprises a substrate, a layer applied to the substrate having a grating structure, an intermediate $SiO_2$ layer deposited on the layer having the grating structures, and a layer of relatively high index of refraction material deposited on the $SiO_2$ layer.

23. The method of claim 21, wherein the grating structure further comprises a substrate, a layer applied to the substrate having the grating structures in the first and second dimensions, an intermediate $SiO_2$ layer deposited on the layer having the grating structures, and a layer of relatively high index of refraction material deposited on the $SiO_2$ layer.

24. The method of claim 22, wherein the SiO2 layer has a thickness of between about 500 and 5000 Angstroms.

25. The method of claim 21, wherein the grating structure in the first dimension has a period of between 260 and about 1500 nm and a depth of the grating between about 100 nm and about 3000 nm, and wherein the grating structure in the second dimension is between about 200 nm and about 1000 nm, and wherein the depth of the grating in the second dimension is between about 10 nm and about 300 nm.

26. The method of claim 1, wherein the sample is deposited on the grating structure in an array of drops and dried forming an array of spots on the grating structure, and wherein a labeled test material is deposited on the array of spots, and wherein label-free measurements of the array of spots are made prior to the depositing of the labeled test material and ER measurements of the array of spots are made after depositing of the labeled test material.

27. The method of claim 26, wherein the label-free measurements comprise obtaining an image of the array of spots and detecting a shift in a peak wavelength value for at least one spot in the array of spots.

* * * * *